US007704508B2

(12) United States Patent
Lobo et al.

(10) Patent No.: US 7,704,508 B2
(45) Date of Patent: Apr. 27, 2010

(54) BABESIA SUBTILISIN

(75) Inventors: Cheryl Lobo, Syosset, NY (US); Estrella Montero, Madrid (ES)

(73) Assignee: New York Blood Center, New York, NY (US)

( * ) Notice: Subject to any disclaimer, the term of this patent is extended or adjusted under 35 U.S.C. 154(b) by 0 days.

(21) Appl. No.: 12/210,900

(22) Filed: Sep. 15, 2008

(65) Prior Publication Data

US 2009/0074783 A1 Mar. 19, 2009

Related U.S. Application Data

(60) Provisional application No. 60/993,787, filed on Sep. 14, 2007.

(51) Int. Cl.
*A61K 39/00* (2006.01)
(52) U.S. Cl. .................. 424/191.1; 530/350; 424/185.1; 424/269.1
(58) Field of Classification Search ....................... None
See application file for complete search history.

(56) References Cited

U.S. PATENT DOCUMENTS

| | | | |
|---|---|---|---|
| 5,591,828 | A | 1/1997 | Bosslet et al. |
| 2003/0118592 | A1 | 6/2003 | Ledbetter et al. |
| 2003/0133939 | A1 | 7/2003 | Ledbetter et al. |

FOREIGN PATENT DOCUMENTS

| | | |
|---|---|---|
| EP | 404097 | 6/1990 |
| WO | 93/11161 | 6/1993 |

OTHER PUBLICATIONS

Mikayama et al. (Nov. 1993. Proc.Natl.Acad.Sci. USA, vol. 90: 10056-10060).*
Rudinger et al. (Jun. 1976. Peptide Hormones. Biol.Council. pp. 5-7).*
Jimenez-Diaz et al, "Improvement of Detection Specificity of Plasmodium-Infected Murine Erythrocytes by Flow Cytometry Using Autofluorescence and YOYO-1", Cytometry Part A 67A: 27-36, 2005.
Lobo, "*Babesia divergens* and *Plasmodium falciparum* Use Common Receptors, Glycophorins A and B, To Invade the Human Red Blood Cell" Infection and Immunity, 2005, 73:649-651.
Withers-Martinez et al, "Subtilisin-like proteases of the malaria parasite", Molecular Microbiology, 2004, 53:55-63.
Huston et al, "Protein engineering of antibody binding sites: Recovery of specific activity in an anti-digoxin single-chain Fv analogue produced in *Escherichia coli*," Proc. Natl. Acad. Sci., USA 1988, 85:5879-5883.
Holliger et al, ""Diabodies": Small bivalent and bispecific antibody fragments," Proc. Natl. Acad. Sci., USA 90:6444-6448, 1993.
Harris et al, "Molecular Identification of a Malaria Merozoite Surface Sheddase", PLoS Pathogens, 1:e29, 2005.
Homer et al, "Babesiosis", Clinical Microbiology Reviews, 2000, 13:451-469.
Persing et al, "Infection with a Babesia-Like Organism in Northern California," the New England Journal of Medicine, 1995, 332:298-303.
Barale et al, "Plasmodium falciparum subtilisin-like protease 2, a merozoite candidate for the merozoite surface protein 1-42 maturase", 1999 Proc. Natl. Acad. Sci., USA, 96:6445-6450.
Liu, et al, "Activity-based protein profiling: the serine hydrolases", PNAS, 1999, 96:14694-14699.
Miller et al, "A Conserved Subtilisin-like Protein TgSUB1 in Microneme Organelles of *Toxoplasma gondii*," The Journal of Biological Chemistry, 2001, 4276:5341-45348.
Blackman et al, "A Subtilisin-like Protein in Secretory Organelles of *Plasmodium falciparum* Merozoites," The Journal of Biological Chemistry, 1998, 273:23398-23409.
Sajid et al, "Maturation and Specificity of *Plasmodium falciparum* Subtilisin-like Protease-1, a Malaria Merozoite Subtilisin-like Serine Protease" J. Biol. Chem., 2000, 275:631-641.
Withers-Martinez et al, "Expression of Recombinant *Plasmodium falciparum* Subtilisin-like Protease-1 in Insect Cells," The Journal of Biological Chemistry, 2002, 277:29698-29709.
Jean et al, "Functional Characterization of the Propeptide of *Plasmodium falciparum* Subtilisin-like Protease-1," The Journal of Biological Chemistry, 2003, 278:28572-28579.
Lantos et al, "Babesiosis: Similar to Malaria But Different, Tick-Borne Diseases in Children," Pediatric Annals 31:192-7, 2002.
Dammin et al, "the Rising Incidence of Clinical Babesia Microti Infection," Human Pathology 12:398-400, 1981.
Ruebush et al, "Human Babesiosis on Nantucket Island," New England J. Med, 297:825-827, 1977.
Hermentin et al, :Erythrocyte Invasion by Malaria (*Plasmodium falciparum*) Merozoites: Recent Advances in the Evaluation of Receptor Sites, Behring Inst. Mitt., 1984, 76:121-141.
Precigout et al, "*Babesia divergens*: Characterization of a 17-kDa Merozoite Membrane Protein," Experimental Parasitology, 1993, 77:425-434.
Holman et al, "A cathepsin L-like cysteine protease is conserved among Babesia equi isolates," Molecular & Biochemical Parasitology, 2002, 119:295-300.

(Continued)

*Primary Examiner*—Jennifer E Graser
(74) *Attorney, Agent, or Firm*—Louis C. Cullman; Michelle S. Glasky; K&L Gates LLP

(57) ABSTRACT

Provided is an isolated and purified protein produced by a naturally occurring *Babesia* sp. comprising an amino acid sequence at least 90% identical to SEQ ID NO:1 and an isolated and purified nucleic acid encoding the above protein. Additionally provided is an isolated and purified nucleic acid comprising at least 20 nucleotides having a sequence 100% identical to a portion of SEQ ID NO:2 or its complement. Further provided is an antibody preparation comprising an antibody that specifically binds to the above protein. Also provided are methods of diagnosing a *Babesia* sp. infection in a mammal, methods of determining whether a blood preparation is contaminated with a *Babesia* sp., methods of determining whether a blood preparation is contaminated with a *Babesia* sp., and methods of treating a mammal infected with a *Babesia* sp., the method comprising inhibiting the production or activity of the protein comprising an amino acid sequence at least 90% identical to SEQ ID NO:1 by the *Babesia* sp. in the mammal. Additionally provided are methods of screening a compound for treating an infection by a *Babesia* sp.

3 Claims, 11 Drawing Sheets

OTHER PUBLICATIONS

Kjemtrup et al, "Human babesiosis: an emerging tick-borne disease," International Journal for Parasitology, 2000, 30:1323-1337.

Kim, "Role of proteases in host cell invasion by *Toxoplasma gondii* and other Apicomplexa," Acta Tropica 2003, 91:69-81.

Carruthers, "Host cell invasion by the opportunistic pathogen," Acta Tropica, 2002, 81:111-122.

Ward et al, "Binding activities of a repertoire of single immunoglobulin variable domains secreted from *Escherichia coli*," Nature, 1989, 341:544-546.

Bird et al, "Single-Chain Antigen-Binding Proteins", Science 1988, 21:423-426.

Barkan et al, "Optimisation of flow cytometric measurement of parasitaemia in plasmodium-infected mice," Int. J. Parisitol. 30:649-53, 2000.

Gorenflot et al, "Cytological and immunological responses to *Babesia divergens* in different hosts: ox, gerbil, man," Parasitology Research, 1991, 77:3-12, 77.

Blackman, "Proteases in host cell invasion by the malaria parasite," Cellular Microbiology, 2004, 6:893-903.

Blackman, "Proteases Involved in Erythrocyte Invasion by the Malaria Parasite: Function and Potential as Chemotherapeutic Targets," Current Drug Targets, 2000, 1:59-83.

Dvorak et al. "Invasion of Erythrocytes by Malaria Merozoites," Science, 187:748-50, 1975.

Garnham, "Human babesiosis: European aspects," Transactions of the Royal Society of Tropical Medicine and Hygiene, 1980, 74:153-155.

Herwaldt et al, "A Fatal Case of Babesiosis in Missouri: Identification of Another Piroplasm That Infects Humans," Annals of Internal Medicine, 1996, 124:643-650.

Spielman et al, "Ecology of Ixodes Dammini-Borne Human Babesiosis and Lyme Disease," Ann. Rev. Entomol., 1985, 30:439-60.

Montero et al, "A conserved Subtilisin Protease Identified in *Babesia divergens* Merozoites," J. Biol. Chem., 2006, 281:35717-35726.

Jack et al, "Mechanisms of Entry of Plasmodia and Babesia into Red Cells," in Babesiosis, (eds. M. Ristic and J.P. Kreier) 1981, pp. 445-457, Academic Press, Inc.

Rudzinska, "Morphologic Aspects of Host-Cell-Parasite Relationships in Babesiosis," in Babesiosis, (eds. M. Ristic and J.P. Kreier) 1981, pp. 87-141, Academic Press, Inc.

Montero et al," "Inhibition of human erythrocyte invasion by *Babesia divergens* using serine protease inhibitors, Molecular & Biochemical Parasitology, 2007, 153:80-84.

Siezen RJ et al. "Subtilases: The superfamily of subtilisin-like serine proteases," Protein Science 6:501-523, 1997.

Dalrymple BP et al. "Characterisation of a family of multi-copy genes encoding rhoptry protein homologs in *Babesia bovis, Babesia ovis* and *Babesia canis*," Mol. Biochem. Parasit. 57:181-192, 1993.

Okubo K et al. "*Babesia bovis*: effects of cysteine protease inhibitors on in vitro growth," Exp. Parasit. 117:214-217, 2007.

* cited by examiner

FIG. 4

```
NC-p65    SAVHTSSRESNDPLLHELKALDPLNMRAAMDILTTAELG-GDRRPLVCVVDTGIDYEHPD 262
TgSUB-1   QSVNTSSKGSNDPLLDRLRGMDALNVKGAWDIITTGEPNNGSRRPLVCVLDTGIDYMHPD 266
PfSUB-1   SESRPGKYHFNDEFRNLQWGLDLSRLDETQRLIN--EHQVMSTR--ICVIDSGIDYMHPD 383
BdSUB-1   TTERPPNGDVKNLFSKDQNYIELLEINRAWNQMR----KMRRKPVKVCIVDTGIDYHHDA 331
                                                  *  *****  *

NC-p65    LRENMEVNQVELHGKPGIDDDNMGKIDDIYGANMVSDSTDPADDHSHGTHVAGTIGARGD 322
TgSUB-1   LRDNMEVNQAERDGTPGVDDDNNGKVDDIYGANMLSKENDPADDHSHGTHVAGTIGAHGN 290
PfSUB-1   LKDNIELNLEELHGRKGPDDDMNGIVDDIYGANFVNNSGNPMDDNYHGTHVSGIISAIGN 443
BdSUB-1   LRDAIELNEMELNGIQGVEDDDNGLIDDIYGANFVDNNMDPMDLNGHGTSLAGIIAAKYK 291
          *     *    *  *  *  ***** *******    *  *  ***  *  *

NC-p65    NGVGIAGIAWAPRLIACKFLNARGRGPDSDALRCINYCAKRGADIMNHSWSGSDAGEALR 382
TgSUB-1   NGIGVAGVAWAPRLLPCKFLAYTGRGYSSDAVRCIDYCVKRGADIVNHSWGGSWPSEALR 368
PfSUB-1   NNIGVVGVDVNSKLIICKALDSRKLGRLGDMFKCLDYCISRMAHMINGSFSFDEYSGIFN 503
BdSUB-1   NPQDIAGINTYARLIPCKAFDSNLSGYLSDILQCIDYCLARGAMVQNHSWTHHKESLALK 351
                     *       *       *  *   *     *  *

NC-p65    QAIEQTAQQGIIHIAAAGNEGR----------DVDVTPNYPAALSTAVSGLITVGNMKM 431
TgSUB-1   EAVVRTANNGLIHIFAAGNDGV----------DIDQRAFYPAAFSTEADGLITVANVKG 417
PfSUB-1   SSVEYLQRKGILFFVSASNCSHPKSSTPDIRKCDLSINAKYPPILSTVYDNVISVANLK- 563
BdSUB-1   SAFAVAEARNVLMVVSVGNVYYQKG-----KRRNIDNHVVPAMYSKYFLNVLTVSGMQV 406

NC-p65    EKQRDGSK--------------------HPSLAESSNYGTKSVQIALPGTDIYSTIPVQS 471
TgSUB-1   DPDHGGKB--------------------IIELDRSSNYGIQRVQVACPGMWILSTVPTSG 477
PfSUB-1   --KNDNNN--------------------HYSLSINSPYSNKYCCQLAAPGTNIYSTAPHN- 599
BdSUB-1   TSEATIREERVERCKLTKPDASCEPSKDLQYELYHKSQFGLSLSQLVAPAYSIHTLNKHN- 465

NC-p65    RPDDPYGWKTSTSMAAPALSGIVALMLAANP---GLSATQIRSILMQSVNETPELSTRVT 528
TgSUB-1   SSQQPYAEKSSTSMAAPALSGIVALMLAVNP---GLSTRQVREGLRQCSVQQPLLQSKVS 568
PfSUB-1   ----SYRKLNGTSMAAPHVAAIASLIFSINP---DLSYKKVIQILKDSIVYLPSLQNMVA 680
BdSUB-1   -----SKVIAESVSMATAIVTGVASLLLSIDMKFLQLTSVSVTHYIRHNIMPLPALKNKVR 551

NC-p65    WGAMPDAKRCLDAALVTPPEGRRPGNPPSHPPPEASPFESSPPDRQHPHPHPPRPNPPEA 588
TgSUB-1   WGSMPDAKRCVEYALTTHASGR---------------------HKSFRREPSTRT 360
PfSUB-1   WAGYADINKAVNLAIKS-------------------------KKTYINSNISNK 354
BdSUB-1   WGGYVNCRATVISMVQYN-------------------------RALAERHKRMKA 376
```

NC-p65 = SEQ ID NO:12
TgSUB-1 = SEQ ID NO:13
PfSUB-1 = SEQ ID NO: 14
BdSUB-1 = SEQ ID NO:1

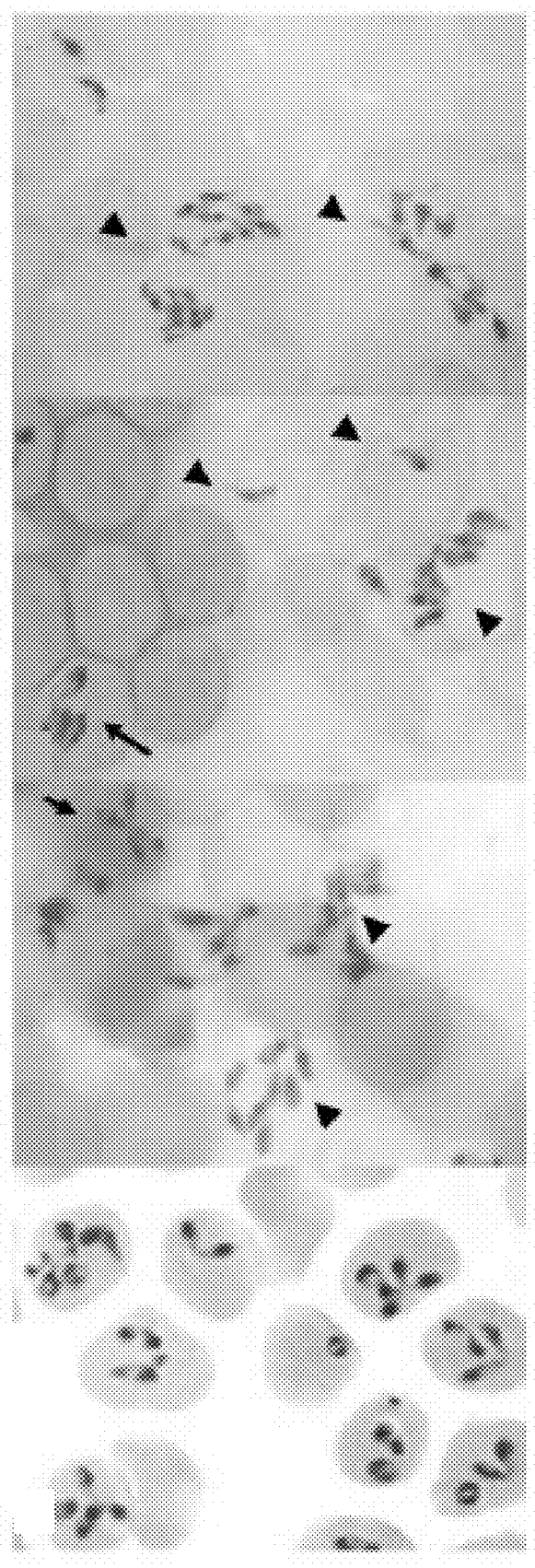

BABESIA SUBTILISIN

CROSS REFERENCE TO RELATED APPLICATIONS

The present application claims the benefit under 35 USC §119(e) to U.S. Provisional Patent Application No. 60/993,787 filed Sep. 14, 2007, the entire contents of which are incorporated by reference herein.

FIELD OF THE INVENTION

The present invention generally relates to Apicomplexan erythrocyte parasites. More specifically, the invention is directed to a *Babesia* protease that is important in erythrocyte invasion.

BACKGROUND OF THE INVENTION

Babesiosis, caused by infection with intra-erythrocytic parasites of the genus *Babesia*, is one of the most common infections of free living animals worldwide and is gaining increasing interest as an emerging zoonosis (a disease communicable from animals to humans). *Babesia* are transmitted by their tick vectors during the taking of a blood meal from the vertebrate host. Babesiosis has long been recognized as an economically important disease of cattle, but only in the last 30 years has *Babesia* been recognized as an important pathogen in man. Human babesiosis is caused by one of several Babesial species that have distinct geographical distributions based on the presence of competent hosts. In North America, babesiosis is caused predominantly by *Babesia* microti, a rodent borne parasite, and also occasionally by two newly recognized species, WA1 and MO-1. In Europe, human babesiosis is considerably rarer but more lethal, and is caused by the bovine pathogen *B. divergens*. The spectrum of disease is broad, ranging from an apparently silent infection to a fulminant, malaria-like disease which can be fatal. When present, symptoms typically are non-specific (fever, headache and myalgia). A number of factors have contributed to the "emergence" of human babesiosis, including increased awareness among physicians, changing ecology, and an increased population of immuno-compromised individuals susceptible to infection. Since 1980, over 500 cases of human infections have been reported.

Parasites that live in red blood cells (RBCs, erythrocytes) have rather ingenious ways of gaining entry to these cells. The best studied is *Plasmodium* spp, the etiological agent of malaria. Like *Plasmodium, Babesia* merozoites enter RBCs using an active invasion process that is mediated by multiple receptor-ligand interactions. The various 'steps' in the invasion process in both *Plasmodium* and *Babesia* have been illustrated using light and electron microscopy and microcinematography. They are identical in both apicomplexans, except for the fact that soon after entry of the *Babesia* merozoite, the parasitophorous vacuolar membrane disappears. The invasion, growth and maturation of both *Plasmodium* and *Babesia* within the human erythrocyte is accompanied by both morphological and biochemical changes in the RBC plasma membrane, which can be attributed to the activity of specific, parasite derived factors. Parasite derived proteases are of particular importance as they play a pivotal role in both the entry and the exit of the parasite by processing both parasite adhesins and host erythrocyte proteins. Serine protease inhibitors can block invasion by *Plasmodium* and *Babesia divergens*. It is therefore hypothesized that serine proteases function during *B. divergens* merozoite invasion, much like they do in *P. falciparum*, in two potential ways: the proteolysis of RBC surface and skeletal proteins and the processing of parasite proteins. Recently the "sheddase" that is responsible for the proteolytic shedding of *P. falciparum* surface proteins during invasion was identified as a membrane bound subtilisin-like protease called PfSUB2.

SUMMARY OF THE INVENTION

The present disclosure is based in part on the discovery of a subtilisin produced by *Babesia* spp. that is important in erythrocyte invasion.

In one embodiment, disclosed herein is an isolated and purified protein produced by a naturally occurring *Babesia* sp. comprising an amino acid sequence at least 90% identical to SEQ ID NO:1 wherein the *Babesia* sp. is selected from the group consisting of *B. divergens, B. microti*, WA1 and MO-1.

In another embodiment, the isolated and purified protein comprises an amino acid sequence at least 95% identical to SEQ ID NO:1, at least 99% identical to SEQ ID NO:1. or 100% identical to SEQ ID NO:1. In another embodiment the isolated and purified protein consists of an amino acid sequence 100% identical to SEQ ID NO:1.

In one embodiment the protein produced by a naturally occurring *Babesia* sp. comprising an amino acid sequence at least 90% identical to SEQ ID NO:1 is BdSUB-1.

In another embodiment, an isolated and purified nucleic acid encoding a protein produced by a naturally occurring *Babesia* sp. is provided wherein the nucleic acid comprises a nucleotide sequence at least 90% identical to SEQ ID NO:2.

In another embodiment, the isolated and purified nucleic acid comprises a nucleotide sequence at least 95% identical to SEQ ID NO:2, at least 99% identical to SEQ ID NO:2 or 100% identical to SEQ ID NO:2. In another embodiment, the isolated and purified nucleic acid consists of a nucleotide sequence 100% identical to SEQ ID NO:2.

In another embodiment, the isolated and purified nucleic acid is provided in a vector capable of transfection into a cell. The cell can be, but is not limited to, a *Babesia* sp. or a bacterium.

In another embodiment, an isolated and purified nucleic acid is provided comprising at least 20 nucleotides having a sequence 100% identical to a portion of SEQ ID NO:2 or its complement.

In yet another embodiment, an antibody preparation is provided comprising an antibody that specifically binds to the protein produced by a naturally occurring *Babesia* sp., wherein the antibody preparation does not comprise an antibody that binds to any protein made by a naturally occurring *P. falciparum*. In one embodiment, the antibody is a monoclonal antibody.

In one embodiment, a method of diagnosing a *Babesia* sp. infection in a mammal is provided, the method comprising determining whether the protein produced by a naturally occurring *Babesia* sp. is present in the blood of the mammal. In another embodiment, the mammal is a human. In yet another embodiment, the *Babesia* sp. is selected from the group consisting of *B. divergens, B. microti*, WA1 and MO-1.

In another embodiment, a method of diagnosing a *Babesia* sp. infection in a mammal is provided, the method comprising determining whether a nucleic acid encoding a protein produced by a naturally occurring *Babesia* sp. comprising a nucleotide sequence at least 90% identical to SEQ ID NO:2 is present in the blood of the mammal.

In another embodiment, a method of determining whether a blood preparation is contaminated with a *Babesia* sp. is provided, the method comprising determining whether the protein produced by a naturally occurring *Babesia* sp (SEQ ID NO:1) or a nucleotide sequence at least 90% identical to SEQ ID NO:2 is present in the blood preparation. In certain embodiments, the blood preparation is donated to a blood bank or from a patient being tested for infection by a *Babesia* sp.

In one embodiment, a method of treating a mammal infected with a *Babesia* sp. is provided, the method comprising inhibiting the production or activity of the protein produced by a naturally occurring *Babesia* sp (SEQ ID NO:1) by the *Babesia* sp. in the mammal. In another embodiment, the protein is BdSUB-1.

In another embodiment of the method, the mammal is treated with an antibody that specifically binds to the protein produced by a naturally occurring *Babesia* sp (SEQ ID NO:1). In another embodiment, the mammal is treated with at least one protease inhibitor that inhibits the activity of the protein.

In another embodiment, the mammal is treated with a nucleic acid. In an embodiment, the nucleic acid is an aptamer, an antisense molecule, a ribozyme, or an RNAi molecule that specifically inhibits production of the protein by the *Babesia* sp.

In yet another embodiment, a method of screening a compound for treating an infection by a *Babesia* sp. is provided, the method comprising determining whether the compound inhibits production or activity of the protein produced by a naturally occurring *Babesia* sp (SEQ ID NO:1) by the *Babesia* sp. In another embodiment, the *Babesia* sp. is selected from the group consisting of *B. divergens, B. microti*, WA1 and MO-1. In another embodiment, the method comprises determining whether the compound inhibits activity of the protein. In another embodiment, the inhibition of activity of the protein is determined by measuring protease activity of the protein in the presence and in the absence of the compound. In another embodiment, the inhibition of activity of the protein is determined by determining whether the compound binds to the protein.

BRIEF DESCRIPTION OF THE DRAWINGS

FIG. 2 depicts the binding of antiserum to the calalytic region of *Plasmodium falciparum* subtilisin (PfSUB1m) to *B. divergens* proteins.

FIG. 3 depicts the cloning and characterization of the bdsub-1 (*Babesia divergens* subtilisin) gene and primary structure of BdSUB-1. The Bd-1 clone identified in the *B. divergens* cDNA expression library and the bdsub-1 gene contain the complete ORF (1701 bp).

FIG. 4 depicts a sequence comparison between apicomplexan subtilisin-1 sequences. Amino acid sequence alignment of the catalytic domains of subtilisins NC-p65 (GenBank Accession Number AAF04257), PfSUB1(GenBank Accession Number CAA05261), TgSUB-1 (GenBank Accession Number AY043483), BdSUB-1 (GenBank Accession Number DQ517294) using the CLUSTAL W method. Residue numbering for each sequence is shown on the right. Positions of identity are indicated by an asterisk and similarity by a dot. Catalytic triad aspartic acid, histidine and serine residues, and oxyanion hole asparagines residue are in bold.

BFA blocked the secretory transport of BdSUB-1 from the ER to the Golgi apparatus, resulting in the accumulation of p55.

Figure 9A:
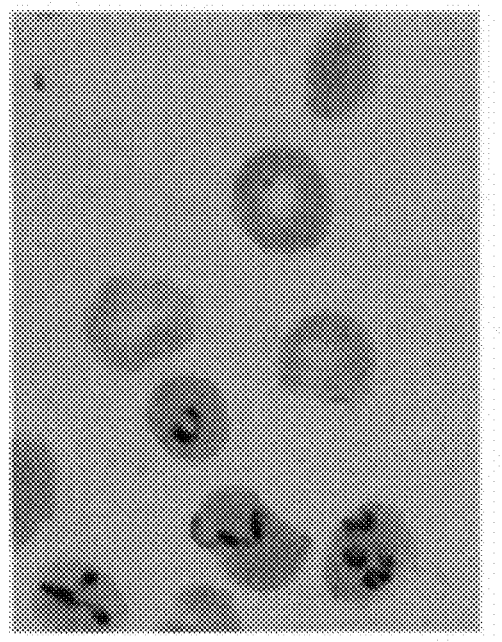
Figure 9B:
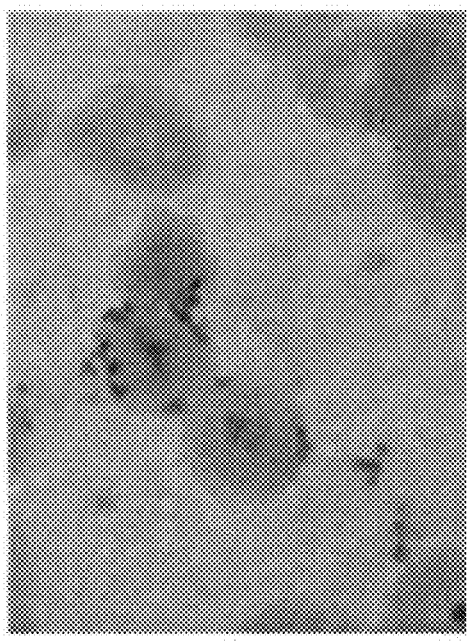
Figure 9C:
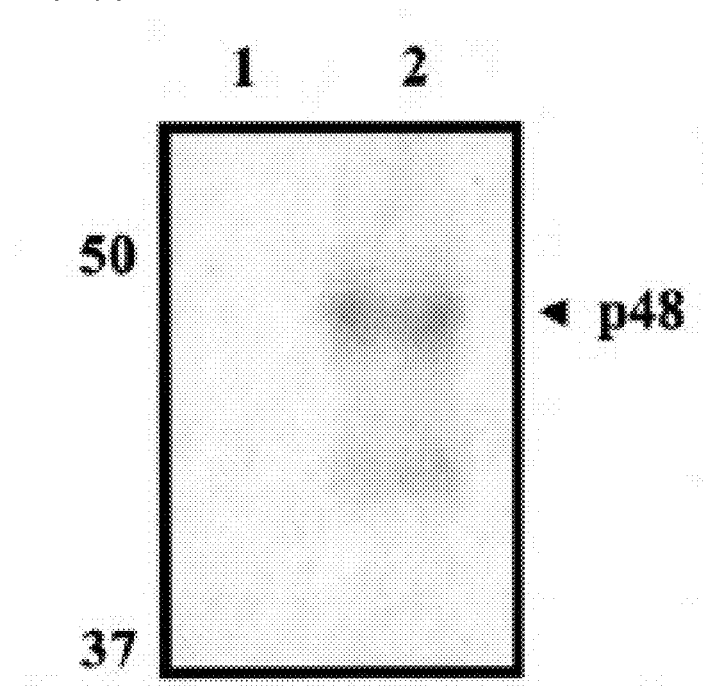

FIG. 9 depicts antibody-stained *B. divergens* merozoites (FIGS. 9A and 9B) and a photograph of a western blot (FIG. 9C) showing that purified anti PFSUB1m antibodies inhibit in vitro invasion of the parasite. Preincubation of *B. divergens* free merozoites with purified PFSUB1m antibodies (100 μg) reduced the efficiency of invasion of erythrocytes by 58%. FIG. 9A depicts Giemsa-stained thin blood smears, showing normal parasite invasion after 8 hours. In FIG. 9B, a high number of free extra-erythrocytic merozoites were visualized in the Giemsa smears of *B. divergens* cultures treated with anti PFSUB1m IgG, after 8 hours. FIG. 9C depicts that BdSUB 1 is secreted into culture supernatants: Parasites were biosynthetically radiolabeled with [$^{35}$S] methionine/cysteine for 9 hours, after which the supernatant was analyzed by immunoprecipitation. Lane 1: Preimmune rabbit sera. Lane 2: PFSUB1m antibodies recognize the 48 kDa active protease and a lower molecular weight fragment in the culture supernatant.

Figure 10A:
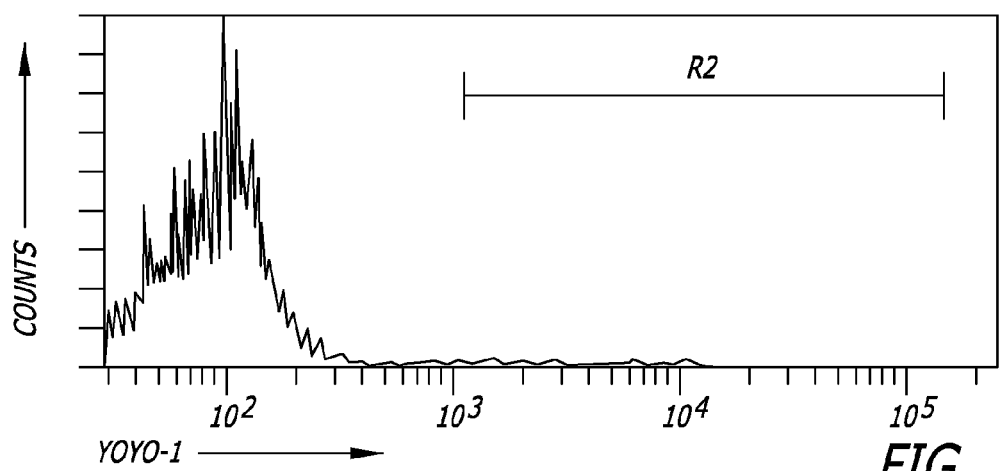
Figure 10B:
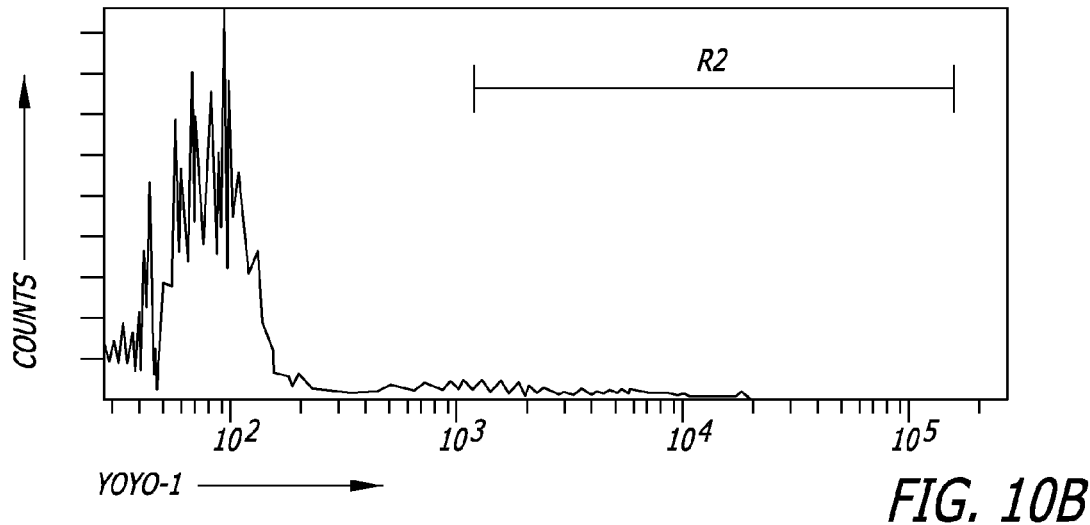
Figure 10C:
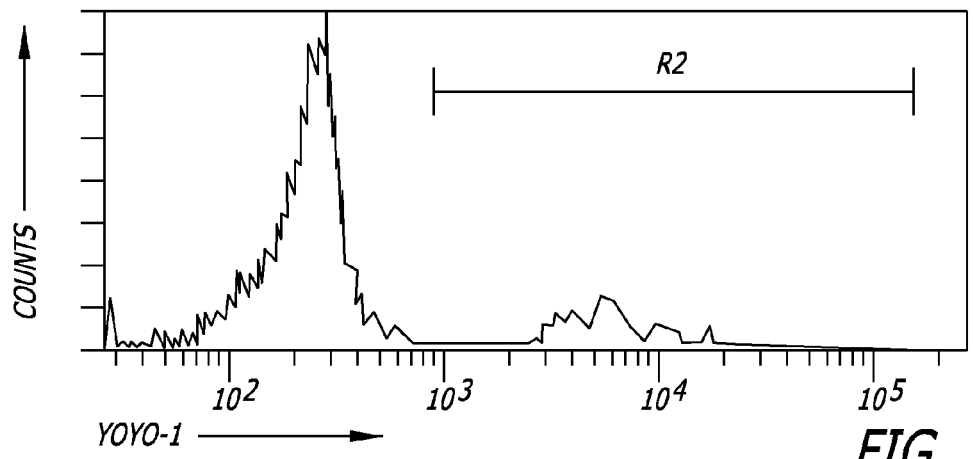
Figure 10D:
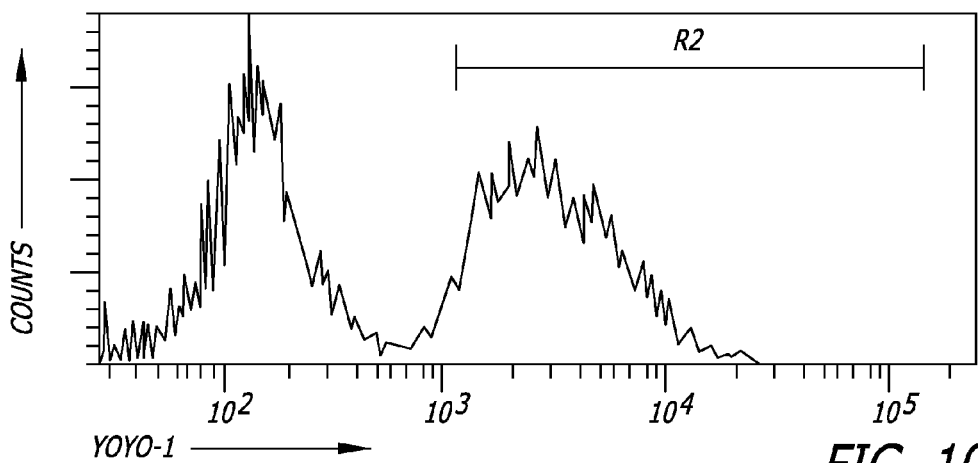
Figure 10E:
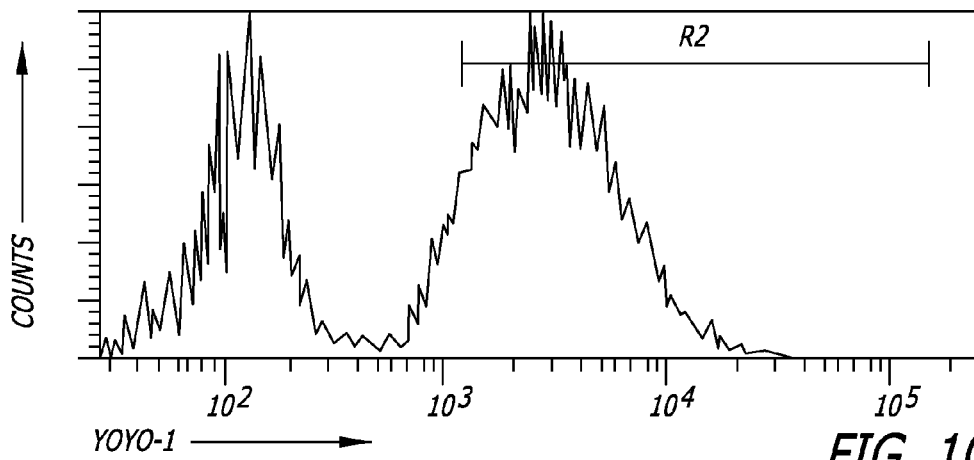
Figure 10F:
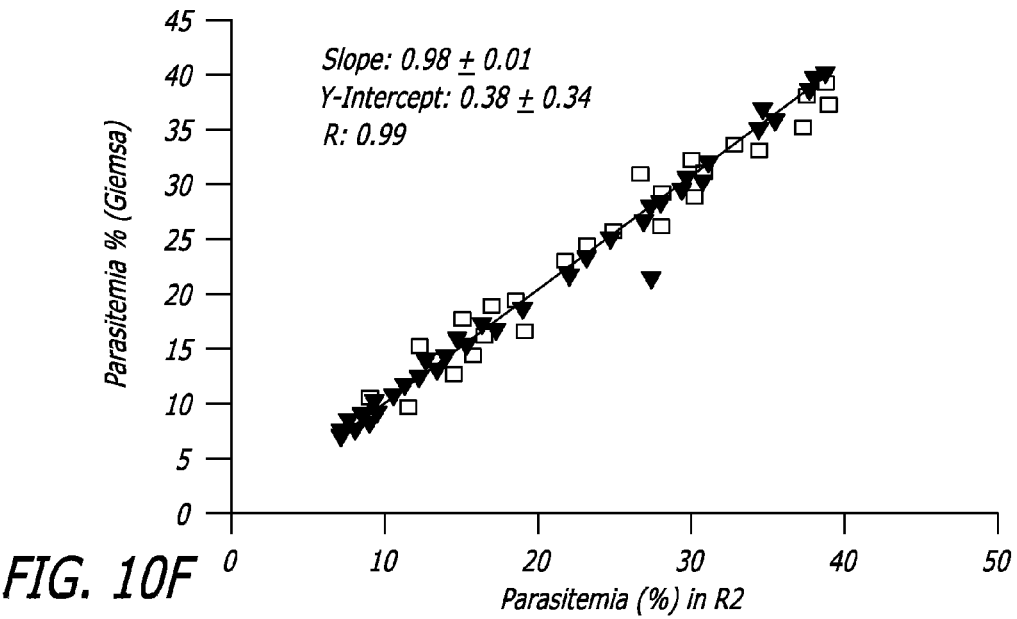

FIG. 10A-10E depicts the evaluation of the parasitemia of *B. divergens* cultures by flow cytometry using the unidimensional YOYO-1 method. Non-infected human RBCs and *B. divergens* infected human RBCs (from culture) were stained with YOYO-1. Histograms depict the infected (R2) versus uninfected (left peak) cells. The fluorescence intensive from the YOYO-1 positive population in relation with the YOYO-1 negative population was measured over 72 hr, the parasitemia was monitored at time 0 and after 10, 48 and 72 h. FIG. 10A: uninfected human RBCs stained with YOYO-1; FIG. 10B: initial parasitemia of 10% in *B. divergens* in vitro culture; FIG. 10C: parasitemia of 19.3% after 10 h; FIG. 10D: parasitemia of 55.7% after 48 h; and FIG. 10E: parasitemia of 65% after 72 h. FIG. 10F depicts the correlation between parasitemia assessed by flow cytometry and light microscopy. Sixty random inhibitor-treated or untreated blood samples were checked by flow cytometry using YOYO-1 or counted after staining with Giemsa (500-1000 cells were counted per slide). The line represents linear regression and its statistical parameters are noted. Parasitemia values determined by flow cytometry are represented by (Δ) and by light microscopy are represented by (□).

Figure 11A:
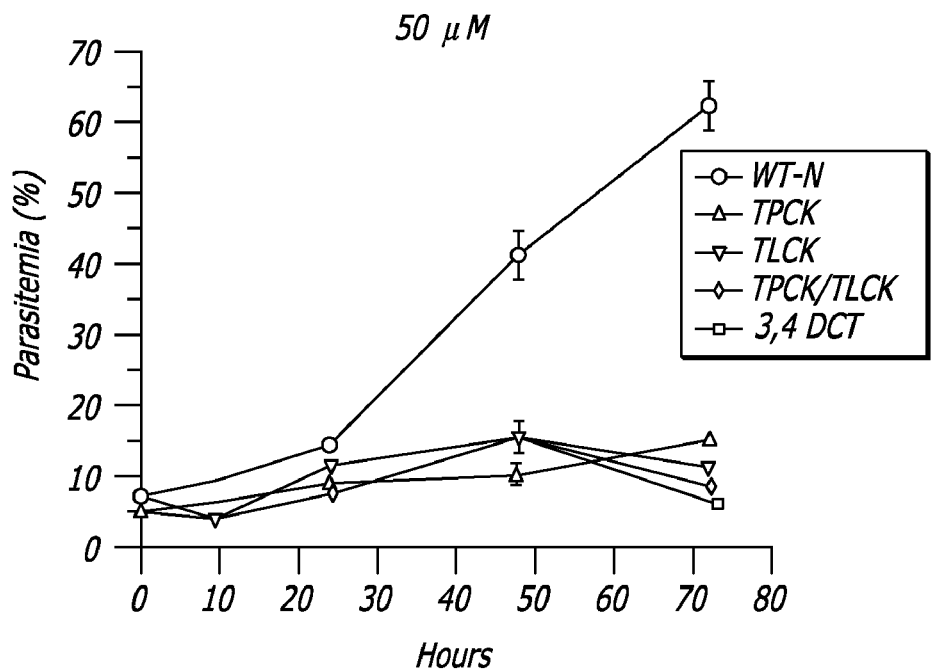
Figure 11B:
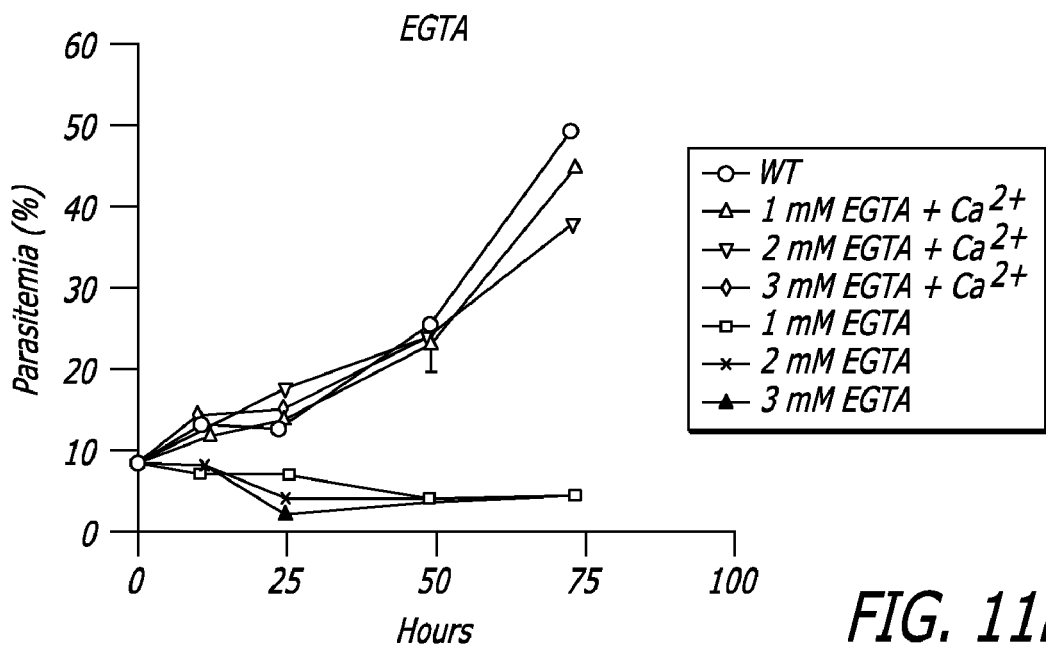

FIG. 11A depicts the inhibitor effect of 50 mM concentration of TPCK, TLCK, a combination of the two compounds (TPCK/TLCK) and 3,4 DCl on *B. divergens* host cell invasion and growth. Parasitemia was monitored at time zero (T0) and 2 h after the end of the first life cycle (T10) and for 24, 48 and 72 h. The percentage of parasitemia at time T0, T10, T24, T48 and T72 was determined by flow cytometry. FIG. 11B depicts the inhibitory effect of tmM, 2 mM or 3 mM EGTA on *B. divergens* host cell invasion and growth in relation to untreated cultures. Also shown is the effect of Ca on EGTA-treated culture parasites. The Ca2+ concentration is the same as the EGTA concentration. Parasitemia was monitored and measured as in FIG. 11A. Each value represents the mean of triplicate samples for each compound standard deviation. WT=wild type. FIG. 11C-11F depicts the effects of protease inhibitors on decreasing successful RBC invasion by *B. divergens*. FIG. 11C depicts Giemsa-stained thin blood smears showing normal invasion of parasites in the absence of inhibitors. A high number of free extra-erythrocyte merozoites (indicated by head arrows) were visualized in the Giemsa smears of *B. divergens* cultures treated with TLCK (FIG. 11D), TPCK (FIG. 11E) or EGTA (FIG. 11F). Arrows indicate infected RBCs.

DEFINITION OF TERMS

The following definition of terms is provided as a helpful reference for the reader. The terms used in this patent have specific meanings as they related to the present invention. Every effort has been made to use terms according to their ordinary and common meaning. However, where a discrepancy exists between the common ordinary meaning and the following definitions, these definitions supersede common usage.

As used herein, the term "antibody" includes intact antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "antigen-binding portion" of an antibody (or simply "antibody portion"), as used herein, refers to one or more fragments of an antibody that retain the ability to bind to an antigen (e.g., a bacterial protein or nucleic acid). It has been shown that the antigen-binding function of an antibody can be performed by fragments of an intact antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546, 1989, incorporated by reference for all it contains regarding dAb fragments), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883; both of which are incorporated by reference for all they contain regarding scFv antibodies). Such single chain antibodies are also intended to be encompassed within the term "antigen-binding portion" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region is preferably modified by replacing one or more cysteine residues with serine residues so as to prevent dimerization. Such binding-domain immunoglobulin fusion proteins are further disclosed in US 2003/0118592 and US 2003/0133939 (incorporated by reference for all they contain regarding binding-domain immunoglobulin fusion proteins). These antibody fragments are obtained using conventional techniques known to those with skill in the art, and the fragments are screened for utility in the same manner as are intact antibodies.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), all of which are incorporated by reference herein for all they contain regarding diabodies.

An antibody that "specifically binds to" or is "specific for" a particular polypeptide or an epitope on a particular polypeptide is one that binds to that particular polypeptide or epitope on a particular polypeptide or protein without substantially binding to any other polypeptide or polypeptide epitope.

Conservative amino acids substitutions are defined as changed, which although they alter the primary sequence of the protein or peptide, do not normally alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, biologically active fragments of the polypeptides are within the scope of the present disclosure.

The term "recombinant human antibody", as used herein, is intended to include all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "administering" includes routes of administration which allow the protein or nucleic acid composition to perform its intended function of treating Babesia infection. Depending on the route of administration, the composition can be coated with or disposed in a selected material to protect it from natural conditions which may detrimentally affect its ability to perform its intended function. The composition can be administered with other bioactive agents and/or with one or more pharmaceutically acceptable carriers. The composition can be administered prior to the onset of septic shock or after the onset of septic shock.

The phrases "parenteral administration" and "administered parenterally" as used herein refers to modes of administration other than enteral and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

As used herein, "pharmaceutically acceptable carrier" includes any and all solvents, dispersion media, coatings, antibacterial and antifungal agents, isotonicity and absorption delaying agents, and the like that are physiologically compatible. Preferably, the carrier is suitable for intravenous, intramuscular, subcutaneous, parenteral, spinal or epidermal administration (e.g., by injection or infusion).

The term "effective amount" or "therapeutically effective amount" of a composition which treats Babesia infections is that amount necessary or sufficient to prevent or treat at least one symptom of Babesia infection. The effective amount can vary depending on such factors as the size and weight of the subject, the type of illnesses, the severity of the symptoms or the particular composition used. One of ordinary skill in the art is able to study the aforementioned factors and make a determination regarding the effective amount of a composition without undue experimentation.

The term "regulatory sequence" is intended to include promoters, enhancers and other expression control elements (e.g., polyadenylation signals) that control the transcription or translation of the antibody chain genes.

The term "identify" refers to nucleic acid or protein sequences which are 100% the same as the reference sequence.

The term "complement," when used in reference to a nucleic acid sequence refers to the property of double-stranded nucleic acids such as DNA and RNA as well as DNA:RNA duplexes. Each strand is complementary to the other in that the base pairs between them are non-covalently connected via two or three hydrogen bonds. Since there is only one complementary base for any of the bases found in DNA and in RNA, one can reconstruct a complementary strand for any single strand. This is essential for DNA replication. For example, the complementary strand of the DNA sequence "A G T C A T G" is "T C A G T A C".

DETAILED DESCRIPTION OF THE INVENTION

The present disclosure is based in part on the discovery of a protease, BdSUB 1, produced by Babesia spp. BdSUB 1 is important in erythrocyte invasion.

The present inventors have isolated and purified a protein produced by a naturally occurring Babesia sp. comprising an amino acid sequence at least 90% identical to SEQ ID NO:1. Any such protein would be expected to have subtilisin activity and be important in erythrocyte invasion of the Babesia sp.

The identification of a novel B. divergens gene, Bdsub-1, that encodes a subtilisin-like serine protease, found in the apically situated dense granules, suggests a function during invasion. This is the first molecular characterization of a protease from any Babesia spp. The B. divergens-human RBC invasion model is an accurate reflection of the invasion process in vivo. It also offers several technical advantages over the malaria culture system for studying different aspects of invasion: the high yield of parasites (>70%), the short life cycle of the parasite (8 h) and the higher infectivity and viability of free merozoites that can be obtained in vitro. The development of the B. divergens—human RBC model offers the ability of directly testing parasite invasion of the RBC, using viable merozoites of B. divergens, which is not feasible with P. falciparum. Thus, the study of proteases participating in B. divergens invasion may also advance our understanding of the biology of P. falciparum invasion.

In one embodiment, the protein comprises an amino acid sequence at least 95% identical to SEQ ID NO:1. In another embodiment, the amino acid sequence is at least 99% identical to SEQ ID NO:1. In yet another embodiment, the protein comprises an amino acid sequence 100% identical to SEQ ID NO:1. In another embodiment, the protein consists of an amino acid sequence 100% identical to SEQ ID NO:1.

```
SEQ ID NO: 1: Babesia divergens subtilisin-1
  1 MVKALRTAFI CIVLAVVNHA LATLDQETPS LSDTTSKDNS TRTPRESPGG SAPNSRDGPN

61 NAASGTKTHA DIIARRLIVR FPYRTKPVPF DDIDLSKYNS SQDDKMGVIV KRLKSLKTYI

121 IEVGEGNSLD EVKRLEDFLI SEGGKVEKDA VAILSGISDK SNTETSASST DAQSPTTERP

181 PNGDVKNLFS KDQWYIELLE INRAWNQMRK MRRKPVKVCI VDTGIDYHHD ALRDAIELNE

241 MELNGIQGVD DDDNGLIDDI YGANFVDNNM DPMDLHGHGT SLAGIIAAKY KNPQDIAGIN

301 TYARLIPCKA FDSNLEGYLS DILQCIDYCL ARGAMVQNHS WTHHKESDAL KSAFAVAEAR

361 NVLMVVSVGN VYYQHGKRRN IDNHVVVPAM YSKYFLNVLT VSGMQVTSEA TIRERVERCK

421 LTKPDASCEP SKDLQYELYH KSQFGLSLSQ LVAPAYSIHT LWKNNSKVIA EGVSMATAIV

481 TGVASLLLSI DMKFLQLTSV SVTHYIRHNI MPLPALKNKV RWGGYVNCRA TVISMVQYNR

541 ALAERHKRMK AMVLPPRKSD KVNIII
```

The protein can be from any Babesia species now known or later discovered. Preferably, the Babesia sp. is a B. divergens. The Babesia sp. can also be, e.g., Babesia microti, a WA1 (B. divergens Washington 1) or an MO-1 (B. divergens Missouri-1).

Also disclosed herein are isolated and purified nucleic acids encoding any of the above proteins. In one embodiment, the nucleic acid comprises a nucleotide sequence at least 90% identical to SEQ ID NO:2. In another embodiment, the nucleic acid comprises a nucleotide sequence at least 95% identical to SEQ ID NO:2. In yet another embodiment, the nucleic acid comprises a nucleotide sequence at least 99% identical to SEQ ID NO:2. In another embodiment, the nucleic acid comprises a nucleotide sequence 100% identical to SEQ ID NO:2. In another embodiment, the nucleic acid consists of a nucleotide sequence 100% identical to SEQ ID NO:2.

SEQ ID NO: 2: *Babesia divergens* subtilisin-1

```
   1 ggcacgaggg gcacatgtcc tgtgtctatc agcataactt cacataacag ctttcgccta
  61 ttgtattcag gattcgtagg tcattcttag cttgtttacg cgcagacact ttgggaaagt
 121 gcgaaacgaa taaggggctc tattgtatgg tgagcggtct atgattgcat gcgatgtgta
 181 aatactaaga tgagtcagac actagtctca ttacgtcact ttgatgaatt cgagacaatg
 241 acagttggac gtcataatca ttggtactta caacacatgc aaatgaaacc aattgacttt
 301 taattcctat ctaaggagcc gcccatacga tggttaaagc tttgagaacc gcgtttattt
 361 gcatcgtgct ggcggtagtc aaccatgccc tggcaacact ggaccaggag acaccttcct
 421 taagtgacac aactagcaaa gataattcaa cccggactcc tcgtgagtcg cctggaggtt
 481 cggcacctaa ctcacgagac ggaccgaata atgcagcaag tgggactaaa acacatgctg
 541 atatcatagc acgccgtcta atcgttaggt tcccttacag aacaaaacct gtaccattcg
 601 atgacataga cctgagcaag tacaattcgt ctcaagacga caaaatgggt gtaatagtca
 661 agaggttgaa atcactcaag acatacataa tagaggtggg agaaggaaat agcctcgatg
 721 aagttaaacg cctagaggat ttcttaatca gtgaaggagg gaaagtggaa aaggatgctg
 781 tagccatttt aagtggtatt agcgataaat ctaacactga aacatctgct tcgagtacgg
 841 atgcacaaag tcccactaca gagaggccac cgaacggcga tgttaagaat ctcttttcaa
 901 aagatcaatg gtacatcgaa ctgttggaga ttaatagagc ctggaatcag atgcggaaaa
 961 tgaggaggaa accggtaaag gtctgcatcg tggacaccgg gatagactat catcatgatg
1021 cattacggga tgcaatagag cttaatgaaa tggaacttaa cggcatccaa ggcgttgatg
1081 acgatgataa tgggctcata gatgacatat atggcgcaaa ctttgtcgac aacaacatgg
1141 atcccatgga ccttcatggt cacggtacaa gtttggcggg cattatagct gccaaatata
1201 agaaccctca ggacatagct ggaattaaca catatgcgcg tctcataccg tgcaaagctt
1261 tcgattcgaa cctggaaggt tatctaagtg atatcttaca atgtattgat tactgcctgg
1321 cacgtggagc catggtccaa aaccacagct ggacgcatca caaagaaagc gatgccctga
1381 agagtgcctt tgcagttgca gaagcacgaa atgtattgat ggtggtttct gttggtaacg
1441 tatattacca acacgggaaa cgaagaaaca ttgacaatca cgtcgtcgta cccgccatgt
1501 acagcaaata tttcctcaat gttttaaccg tatccgggat gcaagttacg agcgaagcta
1561 ccattaggga acgtgtcgag cgatgcaagt taacgaagcc ggacgcttcc tgcgaaccca
1621 gcaaagatct acaatatgaa ctgtaccaca agtctcagtt tgggctttca ctcagccagc
1681 tagtggctcc ggcgtacagt atacacacct tatggaagaa taactctaag gttattgctg
1741 agggggtgtc aatggctact gcaattgtga cgggtgttgc aagtctactt ctttccatag
1801 atatgaagtt cctacaactc acctcagtca gcgtcaccca ctatatacgg cacaacatca
1861 tgccacttcc tgcgcttaag aataaggtga gatggggagg atatgtcaat tgccgtgcga
1921 ctgtaatcag tatggtgcaa tataatagag ccctggctga aaggcacaag agaatgaagg
1981 ccatggttct gccacctagg aaaagtgata aggtcaatat tattatctag ataaaaaaaa
2041 aaaaaaaaaa a
```

In some aspects, the above nucleic acid is in a vector capable of transfection into a cell. Such vectors are well known in the art. The cell can be a prokaryotic cell (e.g., an *E. coli*) or a eukaryotic cell (e.g., a mammalian cell). Preferably, the cell is a *Babesia* sp.

Additionally, disclosed herein are isolated and purified nucleic acids comprising at least 20 nucleotides having a sequence 100% identical to a portion of SEQ ID NO:2 or its complement. Such nucleic acids can be RNA or DNA. These nucleic acids are useful, e.g., as PCR primers, probes for identifying the protein in a mixture of DNA or RNA, miRNAs, antisense molecules, etc.

Also disclosed herein is an antibody preparation comprising an antibody that specifically binds to a protein at least 80% identical to SEQ ID NO:1, where the antibody preparation does not comprise an antibody that binds to any protein made by a naturally occurring *P. falciparum*. These antibodies are useful for detecting the protein, or the *Babesia* that makes the protein. The antibodies can also be used to inhibit activity of the protein and as such can be used therapeutically.

The antibody can be a monoclonal, polyclonal or recombinant antibody or fraction thereof comprising an antibody binding site.

The invention is also directed to methods of diagnosing a *Babesia* sp. infection in a mammal. The methods comprise determining whether a protein at least 80% identical to SEQ ID NO:1 is present in the blood of the mammal. These methods can be used with any mammalian species. Preferably the mammal is a human.

The method can be used to diagnose an infection from any *Babesia* species now known or later discovered. Preferably, the *Babesia* sp. is a *B. divergens*. The *Babesia* sp. can also be, e.g., *Babesia* microti, a WA1 or an MO-1.

The presence of the protein can be determined by any method. In one embodiment, the presence of the protein is determined using an antibody preparation, for example the antibody preparation comprising an antibody that specifically binds to a protein at least 80% identical to SEQ ID NO:1, where the antibody preparation does not comprise an antibody that binds to any protein made by a naturally occurring *P. falciparum*. Non-limiting examples of useful methods using antibodies include western blots, ELISA and dot blots.

Also disclosed are additional methods of diagnosing a *Babesia* sp. infection in a mammal. The methods comprise determining whether a nucleic acid sequence at least 90% identical to SEQ ID NO:2 is present in the blood of the mammal.

The nucleic acid can be identified using any method known in the art, including Southern blots, RNA dot blots, etc. Preferably, the presence of the nucleic acid is determined using a polymerase chain reaction, most preferably using the above-described nucleic acid comprising at least 20 nucleotides having a sequence 100% identical to a portion of SEQ ID NO:2 or its complement.

In another embodiment, methods are provided for determining whether a blood preparation is contaminated with a *Babesia* sp. The methods comprise determining whether a protein at least 80% identical to SEQ ID NO:1 is present in the blood preparation.

Also disclosed herein are methods of determining whether a blood preparation is contaminated with a *Babesia* sp. The methods comprise determining whether a nucleic acid sequence at least 90% identical to SEQ ID NO:2 is present in the blood preparation.

The above methods can be used with any blood preparation, including blood donated to a blood bank, and blood from a patient being tested for infection by a *Babesia* sp.

In another embodiment, methods of treating a mammal infected with a *Babesia* sp are provided. The methods comprise inhibiting the production or activity of a protein at least 80% identical to SEQ ID NO:1 by the *Babesia* sp. in the mammal.

In some aspects of these methods, the mammal is treated with an antibody that specifically binds to the protein. In other aspects, the mammal is treated with a protease inhibitor that inhibits the activity of the protein. The mammal can also be treated with a nucleic acid. An example of such a nucleic acid is an aptamer that specifically binds to the protein. Other examples include an antisense molecule, a ribozyme, or an RNAi molecule that specifically inhibits production of the protein by the *Babesia* sp.

Protease inhibitors suitable for use in treating infections with *Babesia* sp. include, but are not limited to, saquinavir (Hoffman-La Roche), ritonavir (Abbott Laboratories, indinavir (Merck & Co.), nelfinavir (Japan Tobacco), amprenavir (GlaxoSmithKline), lopinavir (Abbott Laboratories), atazanavir, fosamprenavir (GlaxoSmithKline), tipranavir (Boehringer-Ingelheim), darunavir (Tibotec), telaprevir (Vertex), SCH 503034 (Schering-Plough), brecanavir (GlaxoSmithKline), Other protease inhibitors include, but are not limited to, antipain (1-carboxy-2-phenylethyl)carbamoyl-L-arginyl-L-valylargininal), E64 (thyl (2S,3S)-3-[(S)-3-methyl-1-(3-methylbutylcarbamoyl) butylcarbamoyl]oxirane-2-carboxylate), pepstatin, ABSF (4-(2-aminoethyl)benzenesulfonyl fluoride), PMSF (phenylmethylsulfonyl fluoride), TLCK (N-α-tosyl-L-lysine chloromethyl ketone), and TPCK (tosyl phenylalanyl chloromethyl ketone).

Dosages and desired concentrations of pharmaceutical compositions disclosed herein may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. The term "therapeutically effective" amount as used herein refers to the amount needed to perform the particular treatment such as, for example, for treatment or prevention of infection with a *Babesia* sp. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In a preferred embodiment, the disorder is present. In a preferred embodiment, the life of a cell or an individual is prolonged due to the methods described herein.

The compositions provided herein may be administered in a physiologically acceptable carrier to a host. Preferred methods of administration include systemic administration to the host. In one method sustained release vehicles are utilized. The compositions may be administered in conjunction with other compositions for treatment, including but not limited to antibiotics or other bioactive agents.

Also disclosed herein are methods of screening a compound for treating an infection by a *Babesia* sp. The methods comprise determining whether the compound inhibits production or activity of a protein at least 80% identical to SEQ ID NO:1 by the *Babesia* sp.

This method can be used with any *Babesia* sp. Preferably, the *Babesia* sp. is a *B. divergens*. The *Babesia* sp. can also be a *Babesia microti*, a WA1 or an MO-1.

Some aspects of these methods comprise determining whether the compound inhibits activity of the protein. An example of these aspects involves measuring protease activity of the protein in the presence and in the absence of the compound. Another example of these aspects involves determining whether the compound binds to the protein.

Certain embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

A Conserved Subtilisin Protease Identified in Babesia Divergens Merozoites

Invasion of erythrocytes is an integral part of the *Babesia divergens* life cycle. Serine proteases have been shown to play an important role in invasion by related Apicomplexan parasites such as the malaria parasite *Plasmodium falciparum*. Demonstrated here is the presence of two dominant serine proteases in asexual *B. divergens* using a biotinylated fluorophosphonate probe. One of these active serine proteases (p48) and its precursors were recognized by anti-PfSUB1 antibodies. These antibodies were used to clone the gene encoding a serine protease using a *B. divergens* cDNA library. BdSub-1 is a single copy gene with no introns. The deduced gene product (BdSUB-1) clearly belongs to the subtilisin superfamily and shows significant homology to *Plasmodium* subtilisins, with the highest degree of sequence identity around the four catalytic residues. Like subtilisin proteases in other Apicomplexan parasites, BdSUB-1 undergoes two steps of processing during activation in the secretory pathway being finally converted to an active form. The mature protease is concentrated in merozoite dense granules, apical secretory organelles involved in erythrocyte invasion. Anti-PfSUB1 antibodies have a potent inhibitory effect on erythrocyte invasion by *B. divergens* merozoites in vitro. This Example demonstrates conservation of the molecular machinery involved in erythrocyte invasion by these two Apicomplexan parasites and paves the way for a comparative analysis of other molecules that participate in this process in the two parasites.

Experimental Procedures

Parasite propagation. Blood stages cultures of the *B. divergens* (Bd Rouen 1986 strain) were maintained in vitro in human A+RBCs using RPMI 1640 (Invitrogen Corporation) medium supplemented with 10% human serum and sodium bicarbonate solution 7.5% (w/v). Cells were cultured at 37° C. in a 90% $CO_2$, 5% nitrogen and 5% oxygen, as previously described (Gorenflot A. et al. (1991) Parasitol Res 77, 3-1220, incorporated by reference herein for all it contain regarding cell culture).

Purification of free, viable merozoites. Free viable merozoites were purified as previously disclosed (Precigout E et al. (1993) *Exp Parasitol* 77, 425-43421, incorporated by reference herein for all it contains regarding merozoites). Cultures were grown to approximately 60% parasitemia. Infected RBCs and culture supernatants were centrifuged at 300 g for 10 min. The resulting supernatant was first filtered through 5 µm and 1.2 µm reinforced acrylic copolymer membranes (Versapor 3000 and Versapor 1200, Pall Corporation). Filtration was performed at 4° C. to avoid merozoite aggregation. Merozoites were then pelleted at 2000 g for 10 min. 40 ml of supernatant yielded ~108 merozoites. Free merozoites were fixed with 1% paraformaldehyde for electron microscopy or resuspended in Dulbecco's phosphate buffered saline (PBS) and sonicated for western blotting. They were resuspended in RPMI 1640 for use in in vitro growth-inhibitory assays.

Binding of biotinylated fluorophosphonate probe (FP) to parasite proteins. Adapting previous protocols (Liu Y et al., (1999) Proc Natl Acad Sci USA 96, 14694-14699, incorporated by reference herein for all it contains), *B. divergens* infected cells were lysed with 0.15% saponin (equivolume), at 37° C. for 10 min, to release parasites, 5× volume of PBS was added to the suspension and then centrifuged at 3000 rpm for 15 min. The *B. divergens* lysate was prepared in 50 mM Tris-HCl buffer, pH 8.0 and protein concentration adjusted to 1 µg/µl. Two hundred microliters of this lysate was used for the reaction with FP-biotin for 30 min at 25° C. The lysate was incubated for 30 min at 4° C. with one-tenth volume of avidin-agarose beads (Sigma) to deplete endogenous avidin-binding proteins. After a brief centrifugation to pellet the beads, the soluble fraction was removed and supplemented with FP-biotin (prepared as a stock reagent in DMSO) to a final concentration of 2 µM. The reaction was quenched by adding an equal volume of 2×SDS-PAGE buffer before separation on SDS-PAGE and transfer onto nitrocellulose membranes. Blots were blocked in TBS with 1% Tween overnight at 4° C., and probed with an avidin-HRP conjugate (Bio-Rad, 1:2000 dilution) in TBS-Tween with 1% non-fat dry milk for 30 min at 25° C. The blot was washed with TBS-Tween three times (10 min/wash), treated with SuperSignal® chemi-luminescence reagents (Bio-Rad) and exposed to film for 0.1 to 5 min before development.

Production and Immunoscreening of a *B. divergens* cDNA expression library. Total RNA was isolated from cultures with ~60% of parasitemia using Trizol® LS Reagent (Invitrogen) and chloroform extraction. The cDNA synthesis and construction of the library was performed by Lofstrand Labs. The cDNA synthesis was carried out using the Synthesis Kit from Stratagene, the cDNA was column purified to remove species <400 bp, and ligated into EcoRI-XhoI digested zap Express vector (Stratagene). The primary library had >98% recombinants and contained $2 \times 10^6$ pfu. The *B. divergens* cDNA library was screened with polyclonal antibodies specific for the PfSUB1 mature protease domain (PfSUB1m) using standard protocols. Positive clones were purified by the same serum selection procedure and amplified by PCR using T3 and T7 universal primers and the products were sequenced. DNA sequences and predicted amino acid sequence comparisons were carried out with the GenBank+EMBL+DDBJ+PDB and all non-redundant GenBank CDS Translations +PDB+SwissProt+PIR+PRF databases, using BLAST and PSI-BLAST algorithm respectively.

Polymerase Chain reaction (PCR). PCR was carried out using Taq DNA polymerase (Promega). Primers for amplification by PCR of the catalytic domain (3' region of bdsub-1 gene) were BdSub-lcdF (5' ACTACAGAGAGGCCAC-CGAACGGC 3' SEQ ID NO:3) and BdSub-lcdR (5' TCACTTTTCCTAGGTGGCAGAACC 3' SEQ ID NO:4). Primers prepared from bdsub-1 cDNA for amplification by PCR and RT-PCR of a genomic sequence of the bdsub-1 gene and the bdsub-1 ORF, using genomic DNA (gDNA) and total RNA (tRNA) respectively were Bdsub-1F1 (5' AGCCGC-CCATACGATGGTTAAAAGC 3' SEQ ID NO:5) and Bdsub-1R1 (5' ATCTAGATAATAATATTGACCTTATC 3' SEQ ID NO:6). For the PCR, 30 ng of *B. divergens* gDNA was used and 5 µg of tRNA for the RT-PCR. The extension of the 5' end of the bdsub-1 cDNA was obtained by PCR, using standard PCR protocols and maxipools prepared from aliquots of the amplified *B. divergens* expression library. The primer Bdsub-IR2 (5' GGAACTTAACGGCATCCAAGGCGT 3' SEQ ID NO:7) that derives from bdsub-1 cDNA sequence. DNA encoding the putative propeptide of BdSUB-1 was amplified by PCR from the bdsub-1 cDNA using the oligonucleotide primers, PF1 (5' ATGGTTAAAGCTTTGA 3' SEQ ID NO:8) and PR1 (5' CTTAACATCGCCGTTCGG 3' SEQ ID NO:9). The amplified products were subcloned into Topo® TA vector (Invitrogen) for sequencing. The constructs were maintained in the TOP10 *Escherichia coli* strain (Invitrogen) and then sequenced on both strands. All sequencing reactions were performed by the dideoxynucleotide (Sequenase)

method using custom synthesized primers. DNA sequences and predicted amino acid sequence comparisons were performed with the GenBank+EMBL+DDBJ+PDB and all non-redundant GenBank CDS Translations +PDB+SwissProt+ PIR+PRF databases, using BLAST and PSI-BLAST algorithm.

Southern blot analysis. Genomic B. divergens DNA was analyzed by high stringency Southern-blot (65° C.) using a digoxigenin-labeled probe (Roche Applied Science) designed to encompass the catalytic domain (3' region of the gene) by PCR using primer pairs BdSub-lcdF (5' ACTACA-GAGAGGCCACCGAACGGC 3' SEQ ID NO:10) and BdSub-lcdR (5' TCACTTTTCCTAGGTGGCAGAACC 3' SEQ ID NO:11). B. divergens gDNA was digested with a variety of restriction enzymes: XhoI and PstI that do not digest within the gene and SalI, NdeI, HindIII and BglII that digest within the gene. Ten micrograms of each digest was electrophoresed on a 1% agarose gel and transferred to nylon membrane. Following overnight hybridization, the blot was washed twice for 5 min each in 2×SSC and finally for 20 min each in 0.5×SSC at 65° C. Bound probe was detected with Disodium-2-chloro-5(4 methoxyspiro{1,2-dioxetane-3,2'-[5-chloro]tricycle [3.3.1.1.3.7]decan}-4-yl)-1-phenyl phosphate (CDP-Star™, Roche).

Protein Expression and Purification and Antiserum Production. DNA encoding $Leu^{24}$-$Lys^{186}$ of BdSUB-1 was amplified by PCR from bdsub-1 cDNA using the oligonucleotide primers, PF1 5' and PR15' and cloned into the expression plasmid vector pGEX-6T1 (Amersham Biosciences) according to the manufacturer's instructions. *E. coli* strain BL21-gold (DE3) plysS (Stratagene) was transformed with the BdSUB-1p expression plasmid. Two hundred fifty ml of SOB medium containing 100 μg/ml ampicillin (Sigma) was inoculated with 1 ml of fresh overnight culture and grown at 37° C. to $A_{600}$=0.6 prior to induction with 0.2 mM isopropyl-β-D-thiogalactopyranoside. After 4 h of induction, the cells were pelleted and resuspended in B-Per bacterial protein extraction reagent (Pierce) supplemented with a protease inhibitor cocktail that contains 4-(2-aminoethyl)benzenesulfonyl fluoride (AEBSF), pepstatinA, E-64, bestatin, leupeptin, and aprotinin (Sigma) for 10 minutes, the insoluble material was removed by centrifugation and the soluble fraction was used in order to purify the recombinant protein (called BdSUB-1p). The protein was purified using Glutathione Sepharose 4B (Amersham) as described by the manufacturer. Protein concentration was determined by BCA protein assay kit (Pierce).

Polyclonal sera were raised against BdSUB-1p in mice using standard immunization protocols. Briefly, 6 to 8 week old male BALB/c mice were injected subcutaneously with 25 μg of BdSUB-1 p in 0.1 ml of Freund's complete adjuvant (Sigma). Mice were boosted 14 days later with 25 μg of BdSUB-1 in Freund's incomplete adjuvant (Sigma).

SDS-PAGE and Western-blot analysis. For Western-blot assays, cultured parasites were solubilized into three volumes of a saponin buffer (0.15% of saponin in PBS) and incubated at 37° C. for 20 min. Samples were washed with PBS by centrifugation for 5 min and the pellet was resuspended in PBS with a protease inhibitor cocktail (Sigma) and sonicated. Free merozoite lysates were prepared from sonicates of merozoites suspended in PBS and protease inhibitor cocktail (Sigma). After centrifugation, the supernatant was collected and boiled for five minutes in 2× Laemmli sample buffer (Bio-Rad). Samples were run on SDS-PAGE and transferred by electroblotting onto Immuno-Blot™ PVDF membranes, which were blocked in blocking solution: Tris-buffered saline (TBS) with 0.05% Tween-20 (TBS-T) and 3% (wt/vol) Bovine Serum Albumin (BSA).

Blots were incubated with mouse anti-BdSUB-1p antiserum diluted 1:100 in blocking solution, for 1 h at room temperature. Membranes were then treated with horseradish peroxidase conjugate (Pierce, 1:10,000). Blots were washed with washing buffer (0.5 M NaCl, 0.02 M Tris-HCl and 0.05% Tween-20). Antigen detection was by ECL (SuperSignal®WestPico Chemiluminescent Substrate, Pierce).

Electron microscopy. Free *B. divergens* merozoites were fixed with 1% paraformaldehyde and 0.1% glutaraldehyde in 0.1 M cacodylate buffer, for 1 hr at 4° C., washed in 0.1 M buffer, pH 7.4 and treated with 50 mM ammonium chloride to quench remaining aldehydes. The fixed merozoites were then dehydrated and embedded in LR-White Resin (Electron Microscopy Sciences,). Thin sections of embedded parasites were mounted on parlodion covered nickel grids, blocked in 2% BSA and probed with PfSUB I m antibodies overnight at 4° C., washed in buffer containing BSA and Tween 20 and incubated with Goat anti-rabbit IgG conjugated to 6 nm gold particles (Electron Microscopy Science) or Goat-anti-mouse IgG conjugated to 5 nm gold particles (Amersham). After staining with uranyl acetate, sections were observed under a Philips-410 electron microscope (Holland).

Immunoprecipitation. Freshly cultured parasites were washed and resuspended in methionine-free medium (RPMI 1640, MP Biomedicals). Two hundred microcuries $ml^{-1}$ of [$^{35}S$] methionine/cysteine (Perkin Elmer) was added and parasites were incubated at 37° C. for 2 hours. Parasites were lysed in NETT buffer (10 mM Tris pH 7.5, 150 mM NaCl, 0.5 mM EDTA, 0.1% Triton X-100) using a protease inhibitor cocktail (Sigma) and centrifuged to collect the supernatant. Lysates were precleared with protein G (Amersham) before antibody addition. Protein G-Sepharose beads were added and washed extensively with NETTS (10 mM Tris, pH 7.5, 500 mM, NaCl, 5 mM EDTA and 0.1% Triton X-100) and NETT buffers. Protein was eluted from the beads by boiling in sample buffer and run on SDS-PAGE. Gels were stained with Coomassie Blue R-250, fixed with fixing solution (25% isopropanol, 10% acetic acid) for 30 min and enhanced with Amplify™ fluorographic solution (Amersham) for one hour, dried under vacuum and exposed to film for autoradiography.

Monitoring the effect of brefeldin A. The effects of brefeldin A (BFA, Sigma) on BdSUB-1 processing during secretory transport was monitored using $^{35}S$-radiolabeled *B. divergens* cultures. The drug was prepared as a stock solution in methanol at 1 mg $ml^{-1}$ and then added to parasite cultures to a final concentration of 40 μg $ml^{-1}$ BFA. Methanol was added to the control cultures and cells were cultured at 37° C. in a 90% $CO_2$, 5% nitrogen and 5% oxygen for 1 hour. Samples were washed in PBS, lysed in saponin buffer and analyzed by western blot using the anti-PfSUB1m antibodies.

In vitro growth-inhibitory assays (GIA). In order to ensure the antigen specificity of antibody-mediated inhibition, the total preimmune rabbit (PI) and PfSUB1m IgGs were purified using Protein-G Sepharose (Amersham) with IgG binding and elution buffers (Pierce) according to the manufacturer's recommendation and dialyzed with PBS. RPMI supplemented with 10% of human serum and 5% of RBC ($6\times10^8$ RBC) were preincubated at 37° C. in a 90% $CO_2$, 5% nitrogen and 5% oxygen for 30 minutes in 2 cm wells. Purified IgG from PI or PfSUB1m or PBS (control solution) and $2\times10^6$ free merozoites were added to the prewarmed medium in triplicate wells. The final concentration of antibody in the GIA was 100 μg ml-1 in a 1.2 ml final volume. Samples were incubated at 37° C. with 90% $CO_2$, 5% nitrogen, 5% oxygen.

The invasion efficiency was checked after 24 hours and quantitation of parasitemia was performed by counting the total number of intracellular parasites present in $1\times10^4$ RBC at 100× magnification using an Eclipse E 600 microscope (Nikon), after Giemsa staining of smears.

Results

Figure 1A:
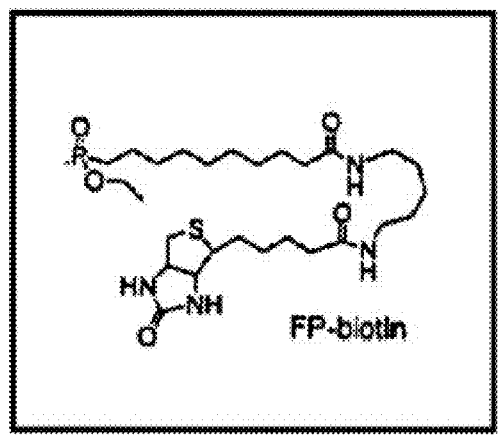
FIG. 1A depicts the chemical structure of FP-biotin (10-(fluoroethoxyphosphinyl)-N-(biotinamidopentyl)decanamide).
Figure 1B:
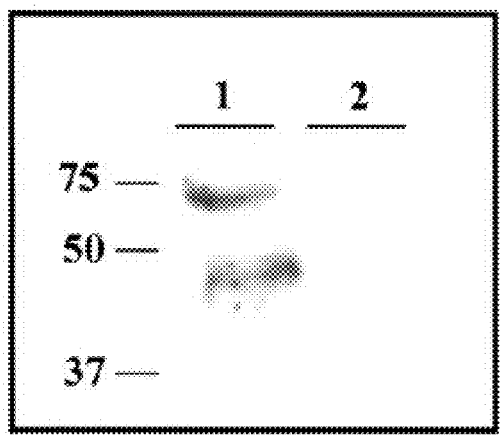
FIG. 1B depicts the identification of serine proteases present in *B. divergens* extracts. Lane 1: FP-biotin identifies 2 major distinct serine proteases in *B. divergens*, of approximately 48 and 75 kDa. Lane 2: Preheated lysate control. Positions of molecular mass standards (in kDa) are shown on the left.

Functional profiling of *B. divergens* serine proteases. A systems level of analysis was applied as the first approach to the study of serine proteases in *B. divergens* invasion. Newly developed, potent, selective probes are available for different classes of proteases that allow simultaneous monitoring of the activities of multiple proteases even in crude protein mixture. The chemical FP probe (FIG. 1A), specifically directed against the active site of serine proteases, identified the expression of all serine proteases present in *B. divergens* crude extracts by virtue of their catalytic activity (FIG. 1B). Two dominant bands of protease activity were detected at ~48 and ~75 kDa, which correspond to two distinct serine proteases. Important controls in this experiment included a parasite extract that was heat denatured before the addition of the probe (lane 2) and also a RBC extract (not shown) to ensure detected protease bands were of *Babesia* origin. Information gathered from the use of this active site directed probe enabled the assessment of the number of dominant serine proteases that exist in the intracellular asexual *B. divergens* parasite.

Figure 2A:
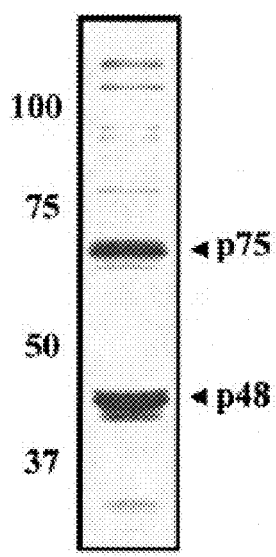
In FIG. 2A, parasite cultures were biosynthetically radiolabeled with [$^{35}$S] methionine/cysteine and then detergent-solubilized and analyzed by immunoprecipitation. The immunoprecipitation with anti-PfSUB1 m identified a 75 kDa (p75) protein and a 48 kDa (p48) protein.
Figure 2B:
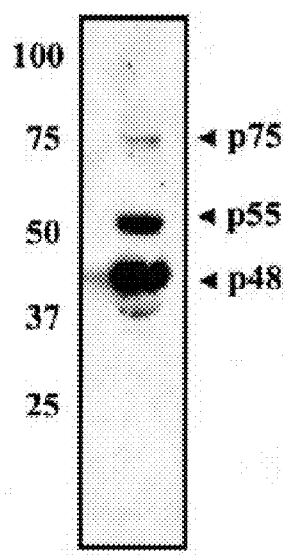
FIG. 2B depicts a western-blot analysis of *B. divergens* saponin lysates subjected to SDS-PAGE under reducing conditions on an 8% gel followed by probing with anti-PfSUB1m antibodies. The antibodies reacted with the dominant p48 band and also with p75 and p55. Positions of molecular mass standards (in kDa) are shown on the left.

Immunoprecipitation and Western blot analysis reveal cross-reactive *B. divergens* subtilisin proteins. Since malaria proteases are likely to act on similar substrates like RBC membrane proteins, tools derived from *P. falciparum* serine proteases were used to identify potential homologues in *B. divergens*. Immunoprecipitation and western blot analysis with the anti-PfSUB1 m antibodies revealed cross-reactive *B. divergens* proteins in the lysates (FIGS. 2A and 2B). A specific dominant band at ~48 kDa (p48) and a minor band at ~75 kDa (p75) were identified by immunoprecipitation (FIG. 2A). Interestingly, both these correspond approximately to the size of the mature protease (47 kDa) and proprotease (82 kDa) forms of PfSUB1 and to the bands detected by FP-biotin (FIG. 1). Western blot analysis with the same antibodies (FIG. 2B) revealed three BdSUB-1 protein bands p75, p48 and a new band of ~55 kDa, not seen in the immunoprecipitation analysis. These results suggested the presence of *B. divergens* subtilisin-like proteases similar to those found in *P. falciparum*.

Cloning of bdsub-1 by immunoscreening of a cDNA expression library. To identify the putative serine protease observed by immunoprecipitation and to demonstrate that it is indeed a subtilisin; a *B. divergens* cDNA expression library was prepared and immuno-screened using the anti-PfSUB1m antiserum. The antibody screening of $1\times10^5$ pfu yielded four immunopositive plaques, each around 2 kB. All four clones were identical. One of these clones (bd-1) was sequenced in both directions and further characterized. Complete sequence analysis of the cDNA clone showed a single contiguous sequence 2051 bp long (SEQ ID NO:2) containing an uninterrupted ORF of 1701 bp encoding a protein (BdSUB-1) of 566 amino acids (SEQ ID NO:1) with an estimated molecular mass of 63,683 Daltons and a isoelectric point of 8.74. To confirm the bdsub-1 ORF, the 5' end of the molecule was amplified by a PCR-cloning approach, using standard PCR protocols and maxi pools prepared from aliquots of the amplified *B. divergens* expression library, as well as primers derived from both the λ-Zap express vector and the known bdsub-1 (T3 and Bdsub-1R2). A fragment of around 1000 bp was amplified, subcloned into Topo® TA vector and sequenced. After analysis of the sequence of the PCR product, the 5'cDNA bdsub-1 together with bd-1 clone confirmed he complete open reading frame (1701 bp) and deduced amino acid sequence of BdSUB-1 protein as well as the nucleotide sequence of neighboring upstream (360 bp) region, shown in FIG. 3A. The initial ATG showed a purine in the −3 position upstream and a guanine in the +4 position downstream as well as 10 stop codons before the initial ATG in the 5'UTR. The entire sequence has been deposited in GenBank (Accession # DQ517294).

Figure 3A:
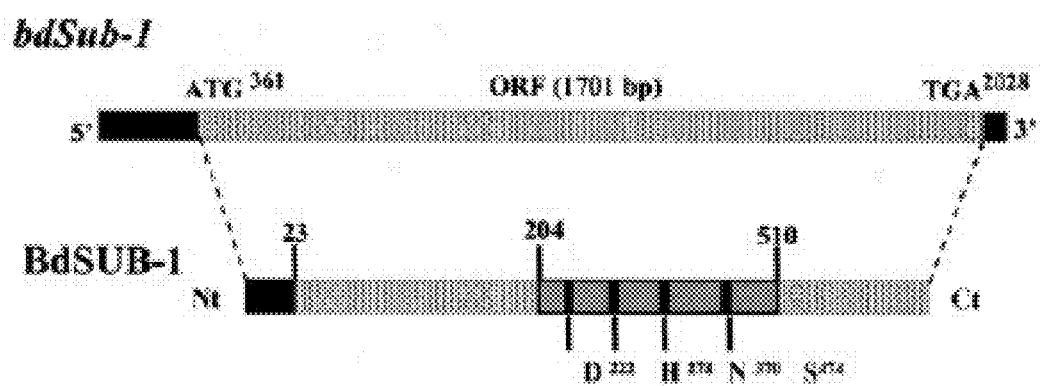
FIG. 3A depicts the bdsub-1 gene. Non-coding regions of the gene are shown in black and coding regions in a shaded box. The structural features of the zymogen BdSUB-1 subtilisin is represented in a shaded bar that includes a signal peptide in black, and a grey region corresponding to the conservative residues into the catalytic domain of BdSUB-1.
Figure 3B:
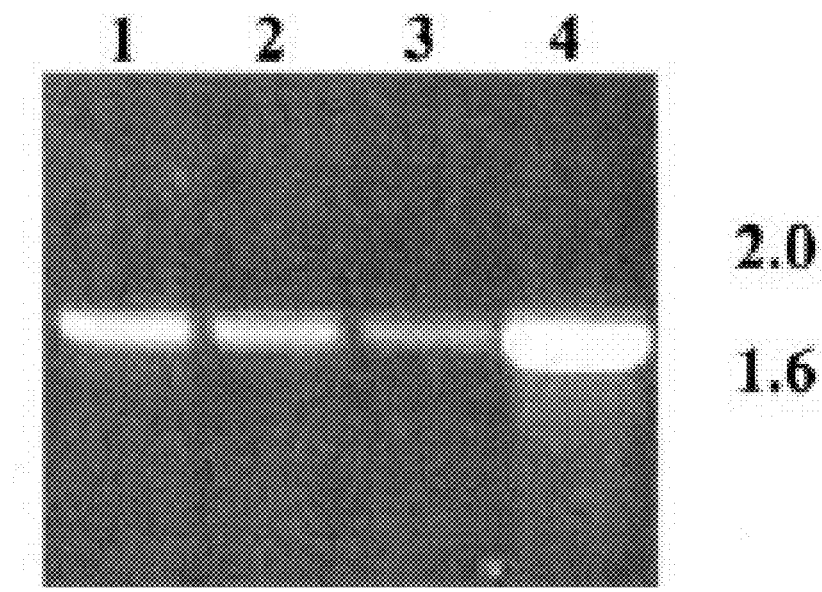
FIG. 3B depicts the cloned of the bdsub-1 gene. The gene was cloned by polymerase chain reaction (PCR) with primers derived from Bd-1 clone. The BdSub-1-F1 forward primer was localized at 5' end upstream before the initial ATG codon and the BdSub-1R1 reverse primer at 3' end upstream of the polyA tail. RT-PCR (reverse transcriptase PCR) carried out using the same primers and *B. divergens* RNA yielded a single 1716 bp fragment in both reactions. The full length Bdsub-1-gDNA and cDNA were cloned into a Topo® TA vector and sequenced. Comparison of genomic and RT-PCR products confirmed the absence of introns in the Bdsub-1 gene. Lane 1:30 ng of gDNA. Lane 2: 20 ng of gDNA. Lane 3: 10 ng of gDNA. Lane 4: 1 μg of *B. divergens* total RNA.

The bdsub-1 gene encodes a subtilisin-type serine protease. PCR amplification of the complete bdsub-1 ORF from total RNA with primers Bdsub-1F1 and Bdsub-1R1, derived from both 5' and 3' ends of Bd1, produced a single DNA fragment of 1716 bp. Amplification from gDNA under the same conditions produced a fragment of the same size (FIG. 3B). The coding region of the cDNA and bdsub-1 gene were cloned into Topo® TA vector and sequenced. The nucleotide sequences of both the products were identical, suggesting that the bdsub-1 gene contains no introns. FIG. 3A depicts a schematic of the gene highlighting the features of the bdsub-1 gene cDNA and deduced protein product. BdSUB-1 belongs to the subtilisin-like (subtilase, S8) protease superfamily. BLAST search of the entire non-degenerate protein databases with the deduced BdSUB-1 protein sequence showed it possesses significant similarity to other known subtilases, particularly those from *P. falciparum* and *P. chabaudi* with 30% identity (scores of 183 and 186 respectively) and a lower score of 150 with a subtilisin of the related apicomplexan *Toxoplasma gondii*. BdSUB-1 also exhibited similar homology to the subtilisin from *Neospora caninum* (NC-p65) having an identity of 31% with a score of 155. The C-terminal 306 as segment ($Ala^{204}$-$Ile^{510}$) was identified as the catalytic domain by PSI-BLAST algorithm with a score of 90.9 and E value of 4e-19. As can be seen from FIG. 4 a high degree of sequence conservation was observed around the catalytic residues, $Asp^{222}$, $His^{278}$ and $Ser^{474}$. Additional conservation was seen at the oxyanion hole residue $Asn^{370}$. By homology with other subtilases, BdSUB-1 could be synthesized as a pre-pro-protease with a putative signal peptide 23 residues long, predicted by SignalP3.0. The signal peptide cleavage site most likely lies between $Arg^{22}$ and $Thr^{23}$. An alignment of BdSUB-1 with sequences from *P. falciparum*, *T. gondii*, *Pseudomonas* sp and *Bacillus* sp suggests that the start of the mature protease could be at $Asn^{187}$ and extend to the C-terminal residue $Ile^{566}$, having a predicted $M_r$ of 42.9 kDa, and the prodomain likely extends from $Leu^{24}$ to $Lys^{186}$ with an estimated $M_r$ of 17.5 kDa. Thus, the theoretical molecular mass of the full-length bdsub-1 gene product (the preproprotease) is 63,683 Da, and that of the proprotease (i.e following signal peptide cleavage) is 62,881 Da. Both these sizes are significantly smaller than the molecular mass of the 75 kDa species detected by immunoprecipitation. However, similar results were obtained for both the *P. falciparum* and *T. gondii* subtilases, where the predicted molecular mass of PfSUB1 preproprotease (77,874 Da) and proprotease (75,066) and that of TgSUB-1 preprotease (84,916 Da) were less than the size detected by immunoprecipitation and pulse-chase experiments.

Figure 5:
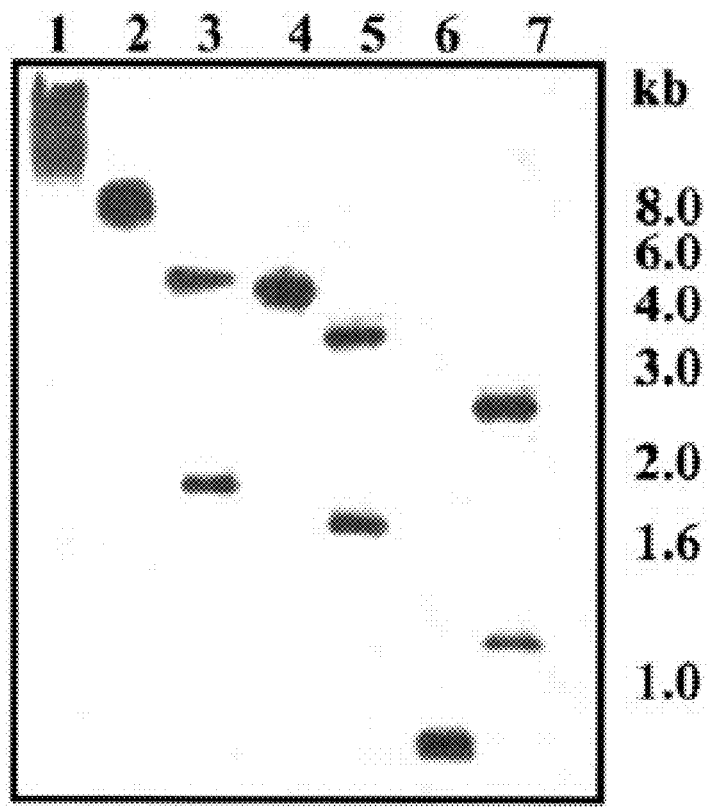
FIG. 5 depicts genomic *B. divergens* DNA analyzed by high stringency Southern-blot using the 3' region of bdsub-1 gene as probe. *B. divergens* gDNA was digested with a variety of restriction enzymes: Xho I and Pst I that do not digest within the gene and Sal I, Nde I, Hind III and Bgl II that digest within the gene. Ten micrograms of each digest was electrophoresed on a 1% agarose gel and transferred to nylon membrane. Following overnight hybridization, the blot was washed under high stringency conditions at 65° C. The results indicate a single copy gene that contains no introns. Lane 1: Undigested gDNA. Lane 2: XhoI-digested gDNA. Lane 3: SalI-digested gDNA. Lane 4: PstI-digested gDNA. Lane 5: NdeI-digested gDNA. Lane 6: HindIII-digested gDNA. Lane 7: BgIII digested gDNA.

The bdsub-1 gene is a single copy gene that contains no introns. To establish the copy number of the bdsub-1 gene, Southern blot analysis of *B. divergens* (Rouen, 1986) strain was performed. *B. divergens* gDNA was digested with restriction enzymes XhoI and PstI (which do not cleave within the bdsub-1 gene), and SalI, NdeI, HindIII and BglII (which cleave within the gene). Digests were probed under high stringency conditions with a probe designed to encompass the catalytic domain (1150 bp 3' region of the gene). The hybridisation patterns obtained indicated that Bdsub-1 is a single copy gene (FIG. 5). The bdsub-1 cDNA contains no PstI site and the Southern blot data therefore indicated that the whole locus could be isolated on a single genomic PstI fragment of about 6 kb (FIG. 5, lane 4).

Figure 6:
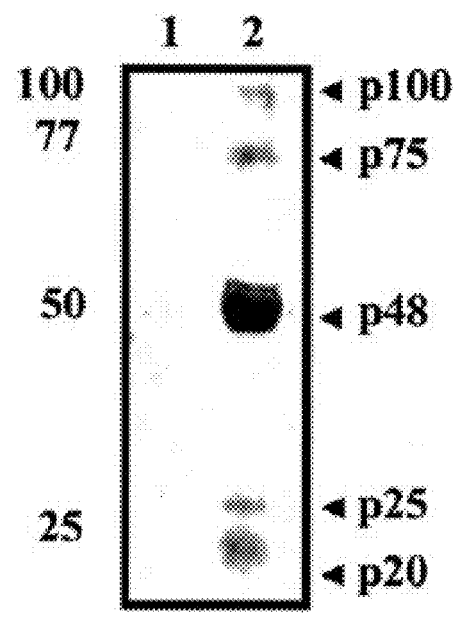
FIG. 6 depicts a western blot showing that anti-BdSUB 1 antiserum recognizes a subtilisin in the *Babesia* parasites. A sonicate of *B. divergens* free merozoites was fractionated by SDS-PAGE, transferred by electroblotting onto PVDF (polyvinylidene fluoride membrane) and probed with anti-BdSUB 1 m antibodies. Lane 1: Negative control using a preimmune rabbit sera. Lane 2: A band of ~48 kDa was clearly identified by the anti-BdSUB 1 m antibodies, another band of ~75 kDa appears with less intensity. Molecular mass markers are shown on the left.

Recombinant expression of BdSUB-1 amino-terminal region in E. coli and production of polyclonal antibodies. The sequence encoding Leu[24] to Lys[186] of BdSUB-1 (BdSUB-1p) was cloned into the expression vector pGEX-6T1 and expressed in E. coli as a GST-fusion protein. The predicted mass of the recombinant product (GST-BdSUB-1p) was ~45 kDa. GST-BdSUB-1p was found to be mostly insoluble. Thus, cells were resuspended in B-Per lysis solution, to solubilize the recombinant protein. The protein was then purified by affinity chromatography on a column of glutathione-agarose. The purified GST-BdSUB-1 p product was analyzed by western-blotting, using an anti-GST monoclonal antibody and used to immunize mice. When the resulting antibodies were used in western-blot assays to probe extracts of free merozoites, a major ~48 kDa protein was recognized. This band thus corresponds to the proteolytically active enzyme. Four less abundant bands of ~100 kDa (p 100), ~75 kDa (p75), ~25 kDa (p25) and ~20 kDa (p20) were also seen (FIG. 6).

Figure 7:
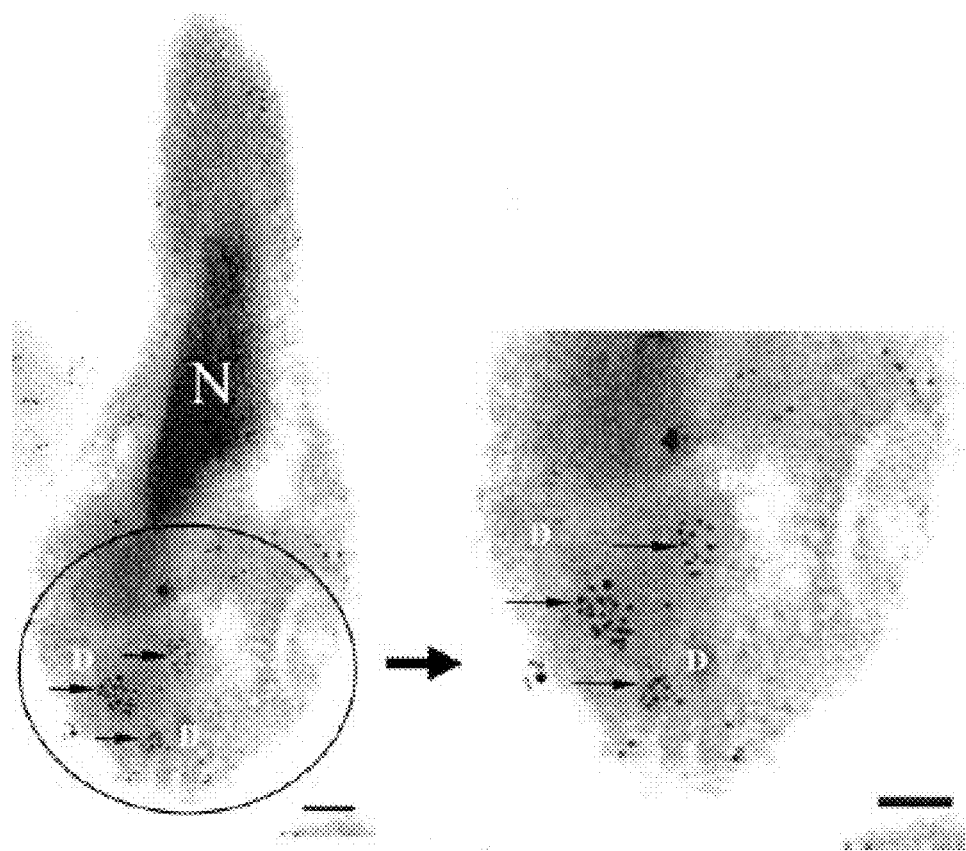
FIG. 7 depicts a micrograph of immunostained merozoites showing that BdSUB-1 localizes to dense granules in the apical region of free *B. divergens* merozoites. Thin sections of resin embedded free merozoites were probed with anti-PFSUB1m antibodies, and then bound antibodies were detected using a gold-labeled anti-rabbit IgG antibody. The nucleus is indicated by (N) and dense granules (D) are marked with arrows. Scale bar is 100 nm.

BdSUB-1 is localized to dense granules. To localize BdSUB-1 within the merozoite, immuno-electron micrographic analysis was carried out on sections of free B. divergens merozoites, using the anti-PfSUB1 m antibodies. As can be seen in FIG. 7, discrete antibody reactivity was observed with circular, electron dense organelles with the morphological characteristics of merozoite dense granules (labeled with arrows in FIG. 7). Immunoreactivity was observed only in the granules situated toward to the apical end of the merozoites. Moreover, p48 was the major bdsub-1 gene product found in Babesia merozoite extracts by western blot and immunoprecipitation and is the final product of BdSUB-1 processing in the parasite. p48 is the protease species that concentrates in the merozoite dense granules. Thus, BdSUB-1 has the same location in merozoites as PfSUB1, indicating that it is a true PfSUB1 homolog. Similar localization in the dense granules was obtained using the anti-BdSUB-1 antibodies, (data not shown).

Figure 8:
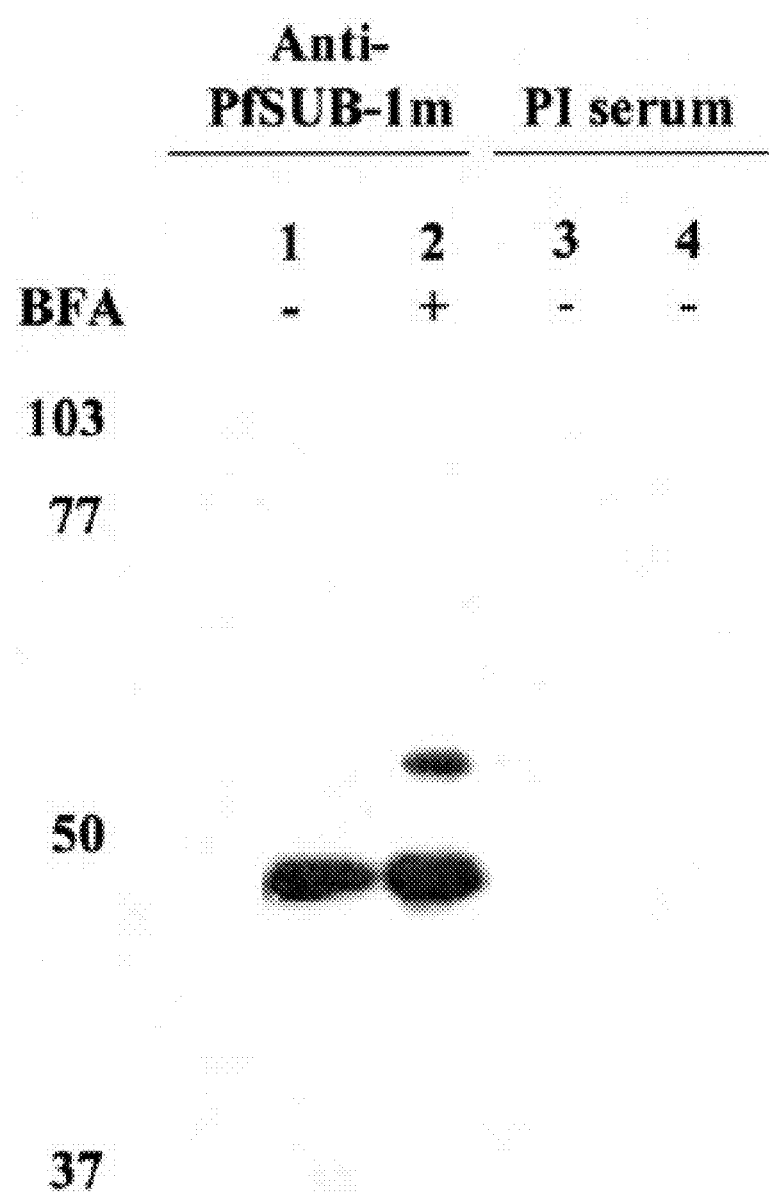
FIG. 8 depicts a western blot showing an analysis of BdSUB-1 processing in parasites in the presence of brefeldin A. Parasites were treated with 40 μg/ml of BFA in methanol (Lane 1) or methanol only (Lane 2) for 1 hour at 37° C. Samples were analyzed by Western-blot using the PfSUB1 m antibodies. Positions of molecular weight markers are shown.

BdSUB-1 undergoes post-translational processing during secretory transport. Subtilases are synthesized as enzymatically inactive zymogens, activation of which invariably requires one or more proteolytic cleavages of the precursor. In order to examine whether BdSUB-1 undergoes intracellular post-translational processing steps within the parasite secretory pathway, brefeldin A (BFA) was employed, which blocks secretory transport of proteins from the endoplasmic reticulum (ER) to the Golgi apparatus. Western-blot analysis was performed on parasite lysates that were obtained from cultures grown in the presence or absence of BFA, using anti-PfSUB1m antibodies. FIG. 8 shows the presence of relatively large amounts of a 55 kDa protein (p55) (lane 2) which was not detected in cultures grown in the absence of BFA. The 48 kDa end-product of BdSUB-1 processing of size (p48) was seen in both lanes 1 and 2. p55 is the BdSub-1 product that accumulated in the ER in the presence of BFA, and p48 in lane 1, represents the already processed BdSUB-1, present in the culture before the use of BFA. Thus, BdSUB-1 is initially synthesized as a large precursor protein of ~78 kDA and cleavage of the signal peptide results in the formation of p75, which is the largest detectable protein seen in the assays. This p75 is then processed to p55, which then gets converted to p48 in the Golgi. Thus, use of BFA interferes with the conversion of p55 to p48, resulting in an accumulation of p55 in BFA treated cultures (FIG. 8 lane 2).

Purified anti-PfSUB1m antibodies inhibit in vitro invasion of the parasite. A B. divergens in vitro inhibition of invasion assay using free merozoites and IgG purified from PfSUB1m antiserum was carried out. Giemsa-stained thin blood smears were prepared and the parasitic growth was monitored after 8 h. Potent inhibition of parasite invasion was observed in these cultures in the presence of both anti-PfSUB1m serum and antibodies purified from this serum (Table 1). The percent of inhibition of invasion of merozoites in the PfSUB1m IgG group was significantly higher than the control (without antibodies) and the IgG purified antibodies from preimmune samples (58% inhibition, with a statistically significant P value of $2 \times 10^{-4}$). On examination of Giemsa smears of parasites grown in the presence of purified IgG from anti-PfSUB1 m serum, a large number of free extra-erythrocytic merozoites were observed by light microscopy (FIG. 9A). This led to the speculation that the antibodies were mediating their inhibition at the time of invasion. Since BdSUB-1 is not localized on the surface of the merozoites, it may be released into the culture supernatant, thus permitting interaction of the antibodies with the subtilisin. To confirm this, radiolabeled culture supernatants were analyzed for the presence of BdSUB-1. Two immunoreactive bands can be clearly seen, corresponding to the 48 kDa active protease and a lower molecular weight band which might represent further processing or degradation of the protein. (FIG. 9B). These results indicate that the protease is secreted from the merozoite at or around the point of invasion, suggesting a role in invasion.

TABLE 1

PfSUB-1 m (purified Ab) inhibits free merozoite invasion
8 h invasion

| B. divergens samples | Mean ± SD | % of invasion relative to the control |
|---|---|---|
| PBS | 1.8 ± 0.2 | 100 |
| PI-purified rabbit Ab | 1.8 ± 0.3 | 100 |
| PfSUB-1-purified rabbit Ab | 0.6 ± 0.05 | 42 |

Inhibition of erythrocyte invasion by B. divergens merozoites with purified Ab against PfSUB1 m.
Values in the first column represent the mean and standard deviation of three independent assays, each performed in triplicate.
Values in the second column represents the % of invasion relative to the control of B. divergens free merozoites used after liberation, and these values were considered 100% for PBS and preimmune purified rabbit antibody.

Babesiosis is fast becoming an important parasitosis because of two factors: (i) that Babesia is now recognized as a zoonotic parasite, with humans acquiring infections from mammalian animal reservoirs; and (ii) that Babesia represents a potential threat to the blood supply for transfusions since asymptomatic infections in humans are common and the spread of parasite via blood transfusions has been frequently reported. Invasion of erythrocytes is an integral part of the Babesia life cycle. The process of invasion by apicomplexan parasites is a carefully coordinated process, involving the regulated release of specialized secretory organelles. Several lines of evidence suggest that proteases are critical for the assembly and trafficking of organellar content proteins. Further, invasion is accompanied by cleavage and shedding of secreted proteins as host cell invasion occurs. Serine protease inhibitors block invasion in Plasmodium and in B. divergens. Proteases may serve a vital role in the infectivity of the Babesia merozoites by hydrolyzing the erythrocyte surface proteins and the complex erythrocyte cytoskeletal network to permit movement of the parasite into and out of the erythrocyte. By virtue of their function, it was hypothesized that they should be conserved in structure among different hemoparasites, particularly between *Plasmodium* and *Babesia*. Since *P. falciparum* and *B. divergens* are harbored by the same host cell, the human RBC, tools derived from studies of the malaria invasion machinery were used to obtain analogous information in *Babesia*. *B. divergens* uses neuraminidase- and trypsin-sensitive receptors, of which glycophorins A and B are the prominent ones, for invasion, similar to *P. falciparum*.

A newly developed functional proteomics tool in the form of chemical probes specifically directed against the active site of serine proteases was used. FP-biotin was used to profile and identify serine proteases in complex crude lysates of the parasite, by virtue of their catalytic activity. Two bands corresponding to potent serine protease activity were detected at ~45 (p48) and ~75 kDa respectively (FIG. 1, lane 1). Interestingly, subtilisin bands of similar molecular weight were seen in immunoprecipitation experiments with anti PfSUB1 m antibodies (FIG. 2A) and anti-PfSUB2 antibodies (data not shown) corresponding to the mature, active enzymes recognized by FP-biotin probe. Using these antibodies against PfSUB1, the gene encoding the corresponding homologous enzyme in *B. divergens* (Bdsub-1) was cloned. Thus, the first known subtilisin protease of this species was identified.

The results presented clearly show that the cloned subtilisin is likely to be proteolytically active during merozoite invasion. BdSUB-1 has a clear homology, overall and within the catalytic domain, with the apicomplexan enzymes PfSUB1 and TgSUB-1 and other subtilisins (identity of ~30%). Notably, BdSUB-1 possesses all of the typical features required of active subtilisins, including the catalytic triad residues essential for proteolytic activity ($Asp^{222}$, $His^{278}$ and $Ser^{474}$) and a glycine residue ($Gly^{472}$) two positions N-terminal to the active site serine. BdSUB-1, also possesses an asparagine ($Asn^{370}$) at the position of the oxyanion hole residue. Other typical features were found including a set of seven cysteine residues within the putative catalytic domain, responsible in a large number of subtilases for disulfide bond formation (35).

The post-translational processing detailed for BdSUB-1 lends support to the idea that it is a functional protease. Subtilases are synthesized as zymogens, which consist minimally of a signal peptide, a propeptide domain and a catalytic domain. By homology with other subtilases, BdSUB-1 is hypothesized to be synthesized as a pre-pro-protein and the processing and maturation scheme (FIG. 3) is very similar to that already described for other apicomplexan subtilisin proteases including PfSUB1 and TgSUB-1. Autocatalytic proteolytic processing is typical in subtilases and represents a mechanism of controlled protease activation in which the inactive precursor or zymogen is converted to an active enzyme only when it reaches an appropriate subcellular compartment. Like subtilisin proteases in other Apicomplexa, BdSUB-1 undergoes two steps of processing during activation in the secretory pathway being finally converted to an active form (p48). Primary processing of BdSUB-1 could take place in the parasite endoplasmic reticulum (ER) where the earliest detectable product may be converted into a 75 kDa form. During the second step, the p75 product probably is truncated, to produce the p48 intracellular processing product that contains the predicted catalytic domain of BdSUB-1 and, according to the FP-biotin results, may represent the mature enzymatically active form of BdSUB-1. This second cleavage may occur during secretory transport from the ER to the Golgi apparatus, since it is inhibited by BFA, p48 is further transported to merozoite dense granules from where it appears to be secreted during host cell invasion. These data indicate that the protease may play a role in invasion. This is supported by results from the antibody mediated inhibition of invasion assay where purified PfSUB1m antibodies dramatically decreased invasion of *B. divergens* and resulted in a significant number of extraerythrocytic free merozoites observed in Giemsa stained smears Taken together, these results indicate a role for BdSUB-1 in erythrocyte invasion.

The conservation of the molecular invasion machinery of the two hemo-parasites *Plasmodium* and *Babesia* paves the way for a comparative analysis of the molecules known to participate in this process. The structure, maturation and substrate specificity of PfSUB1 is known, but its function still remains unknown, mainly because of the difficulties of *P. falciparum* as an experimental system. *B. divergens* could serve as a surrogate model for *Plasmodium* invasion as two of the major difficulties of studying *P. falciparum* invasion can be overcome in the *B. divergens* invasion system, namely, the ease of growing cultures to high parasitemia and the fact that infectious free merozoites can be obtained in the *B. divergens* culture system. BdSUB-1 may be a true functional homolog of PfSUB1 because it shares a common subcellular localization.

Babesiosis has been a largely neglected disease and this study is one of the few to probe mechanisms of host cell entry, results from which may well yield valuable insights into mechanisms of zoonosis.

EXAMPLE 2

Use of Flow Cytometry to Measure *B. Divergens* Parasitemia

Parasitemia for *B. divergens* was assessed in human RBCs using a modification of the methods of Barkan et al. (Int. J. Parasitol. 30:649-53, 2000) and Jimenez-Diaz et al. (Cytometry A 67:27-36, 2005), both of which are incorporated by reference herein for all they contain regarding assessment of parasitemia. DNA content was measured after staining with YOYO-1 (a high affinity cell-impermeant dye that increases green fluorescence by 1000-fold when bound to dsDNA) observed infected erythrocytes compared with non-infected human erythrocytes for *B. divergens*. There was no significant background fluorescence caused by reticulocyte staining or autofluorescence.

To assess the effect of various protease inhibitors, parasitemia was assessed in 180 parasite samples taken at different time points (0 and after 10, 24, 48 and 72 h). In parallel with the evaluation of the parasitemia by FACS (fluorescence activated cell sorting), 60 random parasite samples were analyzed by light microscopy using Giemsa-stained thin blood smears, with 500-1000 RBCs being counted for each smear. FIGS. 10A-E displays histograms of cell counts versus YOYO-1 fluorescence intensities, in which the uninfected cells (left peak) are clearly separated from infected cells (right peak). Integration of the numbers of events represented in the right peak provides a direct estimate of the parasitemia, where one infected cell is one event. A strong linear correlation was observed between results obtained using flow cytometry and the traditional Giemsa stain method (FIG. 10F). Thus, this method presents a fast and sensitive estimation of *B. diver-* gens parasitemia with a differential pattern of staining between *B. divergens* infected and non-infected RBCs.

EXAMPLE 3

TPCK and TLCK Protease Inhibitors are Inhibitors of *B. sivergens* Invasion and Growth Protease inhibitors were tested for their ability to inhibit the invasion and growth of *B. divergens* in vitro. The treatment of the *B. divergens* parasites with antipain (1-carboxy-2-phenylethyl)carbamoyl-L-arginyl-L-valylargininal, antipromotor), E64 (thyl (2S,3S)-3-[(S)-3-methyl-1-(3-methyl butylcarbamoyl) butylcarbamoyl]oxirane-2-carboxylate, inhibitor of cysteine proteases), pepstatin (CAS #26305-03-3, inhibitor of aspartic proteases), ABSF (4-(2-aminoethyl) benzenesulfonyl fluoride, hydrophilic serine protease inhibitor) or PMSF (phenylmethylsulfonyl fluoride, inhibitor of serine and cysteine proteases) showed minimal to moderate effects on parasite invasion (2-38% inhibition, Table 2) and growth (9-47%, Table 2). However, TLCK (N-α-tosyl-L-lysine chloromethyl ketone, irreversible serine protease inhibitor) and TPCK (tosyl phenylalanyl chloromethyl ketone, irreversible inhibitor of chymotrypsin) demonstrated more pronounced effects on both *B. divergens* invasion (Table 2) and growth (FIG. 11A) at concentrations of 50 and 100 μM. Inhibition of invasion using TPCK was approximately 65%, and after 72 h parasitemia was decreased by 86%, compared to control wells (FIG. 11A). For a second serine protease inhibitor, TLCK, and approximate 60% inhibition of invasion was seen relative to invasion in the absence of TLCK and this inhibition was increased after 72 h to a growth inhibition of approximately 90% (FIG. 11B). Inhibitor effects of these inhibitors were significant for the in vitro invasion and growth of *B. divergens* at concentrations at both 50 and 100 μM (P<0.05) as compared to the parasite growth in the presence of DMSO (dimethyl sulfoxide).

A striking observation in the TPCK and TLCK treated cultures was a large number of extracellular merozoites seen around the host RBCs, on examination by microscopy in the cultures of *B. divergens* (FIGS. 11D and 11E) which are the parasites that did not successfully mediate invasion. Although TPCK and TLCK significantly suppressed parasitemia during the invasion and growth inhibition assay, there was no alteration in the morphology of the parasites and these inhibitors did not destroy the parasites. 3,4 DCI (irreversible inhibitor of serine proteases) used at 50 and 100 μM, led to 40% inhibition of invasion and 76% on growth compared to control (FIG. 11A). The parasitemia of the samples containing DMSO (negative control) showed no significant difference from the control culture (wild type without DMSO control).

Thus, using a wide variety of relatively broad-spectrum protease inhibitors on the invasion and growth of *B. divergens* in culture, of the different categories of inhibitors, those specific for serine proteases had the greatest impact on both the invasion and growth of *B. divergens*.

TABLE 2

Inhibitory effect of protease inhibitors on *B. divergens* erythrocyte invasion and growth.

| Inhibitor | Invasion | | Growth | |
|---|---|---|---|---|
| | T10 50 μM | T10 100 μM | T72 50 μM | T72 100 μM |
| Antipain | 33.0 ± 6.5 | 37.7 ± 14.1 | 15.0 ± 8.4 | 16.0 ± 8.5 |
| E64 | 9.0 ± 9.0 | 33.0 ± 4.7 | 3.5 ± 3.0 | 21.7 ± 6.5 |
| ABSF | 3.3 ± 6.8 | 34.0 ± 9.0 | 8.8 ± 7.4 | 28.0 ± 5.0 |
| PMSF | 28.0 ± 8.9 | 35.0 ± 18.0 | 45.0 ± 5.2 | 46.7 ± 3.3 |
| Pepstatin | 17.0 ± 6.4 | 2.0 ± 0.8 | 9.1 ± 3.1 | 16.0 ± 9.2 |
| TPCK | 64.0 ± 3.1 | 66.0 ± 1.2 | 89.0 ± 2.9 | 93.0 ± 2.6 |
| TLCK | 64.0 ± 3.1 | 60.0 ± 2.0 | 92.1 ± 3.0 | 94.1 ± 0.9 |
| 3,4 DCI | 38.0 ± 2.0 | 43.0 ± 1.2 | 70.7 ± 1.4 | 76.0 ± 2.3 |
| | 1 mM | 3 mM | 1 mM | 3 mM |
| EGTA | 48.0 ± 3.1 | 52.0 ± 2.6 | 82.0 ± 0.4 | 83.0 ± 0.5 |

EXAMPLE 3

Effect of Calcium on *B. divergens* Invasion and Growth

Through the use of chelating agents, it has been shown that extracellular calcium is indispensable to the intra-erythrocytic life cycle of *P. falciparum*. The attachment and invasion by *P. knowlesi* was greatly reduced in the presence of EDTA (ethylenediaminetetraacetic acid) or EGTA (ethylene glycol tetraacetic acid). In *Babesia cabali*, calcium also inhibits erythrocyte invasion.

The effects of EGTA, a chelating agent capable of binding metal ions including $Ca^{2+}$, on the invasion and growth of *B. divergens* was tested. EGTA cannot permeate the biological membrane of cells so its effects are only on the chelation of extracellular ions. As many serine proteases require $Ca^{2+}$ for activity, EGTA also functions as a serine protease inhibitor. Inhibitor effects of EGTA were found to be significant for the in vitro invasion (Table 2) and growth (FIG. 11B) of *B. divergens* at concentrations of 1, 2 and 3 mM (P<0.05) as compared to the controls. Using light microscopy, a high percentage of extracellular merozoites were detected on smears of parasites cultured in the presence of all concentrations of EGTA (FIG. 11F). This inhibition of invasion and growth by EGTA was completely reversed by the addition of $Ca^{2+}$ in the same concentration as EGTA. No difference in invasion or growth pattern was detected between the culture containing different concentrations of $Ca^{2+}$ without EGTA and the control culture. The percentage of inhibition on invasion by EGTA was 50% (Table 2). The effect of EGTA on growth of the parasite, measured after 72 h was 83% lower than the control parasite (FIG. 11B). Thus, $Ca^{2+}$ is essential for both invasion and growth of *B. divergens*.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An isolated and purified protein produced by a naturally occurring *Babesia divergens* comprising an amino acid sequence at least 90% identical to SEQ ID NO:1.

2. An isolated and purified protein produced by a naturally occurring *Babesia divergens* comprising an amino acid sequence at least 95% identical to SEQ ID NO: 1.

3. An isolated and purified protein produced by a naturally occurring *Babesia divergens* comprising an amino acid sequence at least 99% identical to SEQ ID NO:1.

* * * * *

SEQUENCE LISTING

```
<160> NUMBER OF SEQ ID NOS: 14

<210> SEQ ID NO 1
<211> LENGTH: 566
<212> TYPE: PRT
<213> ORGANISM: Babesia divergens

<400> SEQUENCE: 1

Met Val Lys Ala Leu Arg Thr Ala Phe Ile Cys Ile Val Leu Ala Val
1               5                   10                  15

Val Asn His Ala Leu Ala Thr Leu Asp Gln Glu Thr Pro Ser Leu Ser
            20                  25                  30

Asp Thr Thr Ser Lys Asp Asn Ser Thr Arg Thr Pro Arg Glu Ser Pro
        35                  40                  45

Gly Gly Ser Ala Pro Asn Ser Arg Asp Gly Pro Asn Asn Ala Ala Ser
    50                  55                  60

Gly Thr Lys Thr His Ala Asp Ile Ile Ala Arg Arg Leu Ile Val Arg
65                  70                  75                  80

Phe Pro Tyr Arg Thr Lys Pro Val Pro Phe Asp Asp Ile Asp Leu Ser
                85                  90                  95

Lys Tyr Asn Ser Ser Gln Asp Asp Lys Met Gly Val Ile Val Lys Arg
            100                 105                 110

Leu Lys Ser Leu Lys Thr Tyr Ile Ile Glu Val Gly Glu Gly Asn Ser
        115                 120                 125

Leu Asp Glu Val Lys Arg Leu Glu Asp Phe Leu Ile Ser Glu Gly Gly
    130                 135                 140
```

-continued

```
Lys Val Glu Lys Asp Ala Val Ala Ile Leu Ser Gly Ile Ser Asp Lys
145                 150                 155                 160

Ser Asn Thr Glu Thr Ser Ala Ser Ser Thr Asp Ala Gln Ser Pro Thr
                165                 170                 175

Thr Glu Arg Pro Pro Asn Gly Asp Val Lys Asn Leu Phe Ser Lys Asp
            180                 185                 190

Gln Trp Tyr Ile Glu Leu Leu Glu Ile Asn Arg Ala Trp Asn Gln Met
        195                 200                 205

Arg Lys Met Arg Arg Lys Pro Val Lys Val Cys Ile Val Asp Thr Gly
    210                 215                 220

Ile Asp Tyr His His Asp Ala Leu Arg Asp Ala Ile Glu Leu Asn Glu
225                 230                 235                 240

Met Glu Leu Asn Gly Ile Gln Gly Val Asp Asp Asp Asn Gly Leu
                245                 250                 255

Ile Asp Asp Ile Tyr Gly Ala Asn Phe Val Asp Asn Asn Met Asp Pro
            260                 265                 270

Met Asp Leu His Gly His Gly Thr Ser Leu Ala Gly Ile Ile Ala Ala
        275                 280                 285

Lys Tyr Lys Asn Pro Gln Asp Ile Ala Gly Ile Asn Thr Tyr Ala Arg
    290                 295                 300

Leu Ile Pro Cys Lys Ala Phe Asp Ser Asn Leu Glu Gly Tyr Leu Ser
305                 310                 315                 320

Asp Ile Leu Gln Cys Ile Asp Tyr Cys Leu Ala Arg Gly Ala Met Val
                325                 330                 335

Gln Asn His Ser Trp Thr His His Lys Glu Ser Asp Ala Leu Lys Ser
            340                 345                 350

Ala Phe Ala Val Ala Glu Ala Arg Asn Val Leu Met Val Val Ser Val
        355                 360                 365

Gly Asn Val Tyr Tyr Gln His Gly Lys Arg Arg Asn Ile Asp Asn His
    370                 375                 380

Val Val Pro Ala Met Tyr Ser Lys Tyr Phe Leu Asn Val Leu Thr
385                 390                 395                 400

Val Ser Gly Met Gln Val Thr Ser Glu Ala Thr Ile Arg Glu Arg Val
                405                 410                 415

Glu Arg Cys Lys Leu Thr Lys Pro Asp Ala Ser Cys Glu Pro Ser Lys
            420                 425                 430

Asp Leu Gln Tyr Glu Leu Tyr His Lys Ser Gln Phe Gly Leu Ser Leu
        435                 440                 445

Ser Gln Leu Val Ala Pro Ala Tyr Ser Ile His Thr Leu Trp Lys Asn
    450                 455                 460

Asn Ser Lys Val Ile Ala Glu Gly Val Ser Met Ala Thr Ala Ile Val
465                 470                 475                 480

Thr Gly Val Ala Ser Leu Leu Leu Ser Ile Asp Met Lys Phe Leu Gln
                485                 490                 495

Leu Thr Ser Val Ser Val Thr His Tyr Ile Arg His Asn Ile Met Pro
            500                 505                 510

Leu Pro Ala Leu Lys Asn Lys Val Arg Trp Gly Gly Tyr Val Asn Cys
        515                 520                 525

Arg Ala Thr Val Ile Ser Met Val Gln Tyr Asn Arg Ala Leu Ala Glu
    530                 535                 540

Arg His Lys Arg Met Lys Ala Met Val Leu Pro Pro Arg Lys Ser Asp
545                 550                 555                 560
```

-continued

Lys Val Asn Ile Ile Ile
565

<210> SEQ ID NO 2
<211> LENGTH: 2051
<212> TYPE: DNA
<213> ORGANISM: Babesia divergens

<400> SEQUENCE: 2
ggcacgaggg gcacatgtcc tgtgtctatc agcataactt cacataacag ctttcgccta 60
ttgtattcag gattcgtagg tcattcttag cttgtttacg cgcagacact ttgggaaagt 120
gcgaaacgaa taaggggctc tattgtatgg tgagcggtct atgattgcat gcgatgtgta 180
aatactaaga tgagtcagac actagtctca ttacgtcact ttgatgaatt cgagacaatg 240
acagttggac gtcataatca ttggtactta caacacatgc aaatgaaacc aattgacttt 300
taattcctat ctaaggagcc gcccatacga tggttaaagc tttgagaacc gcgtttattt 360
gcatcgtgct ggcggtagtc aaccatgccc tggcaacact ggaccaggag acaccttcct 420
taagtgacac aactagcaaa gataattcaa cccggactcc tcgtgagtcg cctggaggtt 480
cggcacctaa ctcacgagac ggaccgaata atgcagcaag tgggactaaa acacatgctg 540
atatcatagc acgccgtcta atcgttaggt tcccttacag aacaaaacct gtaccattcg 600
atgacataga cctgagcaag tacaattcgt ctcaagacga caaaatgggt gtaatagtca 660
agaggttgaa atcactcaag acatacataa tagaggtggg agaaggaaat agcctcgatg 720
aagttaaacg cctagaggat ttcttaatca gtgaaggagg gaaagtggaa aaggatgctg 780
tagccatttt aagtggtatt agcgataaat ctaacactga aacatctgct tcgagtacgg 840
atgcacaaag tcccactaca gagaggccac cgaacggcga tgttaagaat ctcttttcaa 900
aagatcaatg gtacatcgaa ctgttggaga ttaatagagc ctggaatcag atgcggaaaa 960
tgaggaggaa accggtaaag gtctgcatcg tggacaccgg gatagactat catcatgatg 1020
cattacggga tgcaatagag cttaatgaaa tggaacttaa cggcatccaa ggcgttgatg 1080
acgatgataa tgggctcata gatgacatat atggcgcaaa ctttgtcgac aacaacatgg 1140
atcccatgga ccttcatggt cacggtacaa gtttggcggg cattatagct gccaaatata 1200
agaaccctca ggacatagct ggaattaaca catatgcgcg tctcataccg tgcaaagctt 1260
tcgattcgaa cctggaaggt tatctaagtg atatcttaca atgtattgat tactgcctgg 1320
cacgtggagc catggtccaa aaccacagct ggacgcatca caaagaaagc gatgccctga 1380
agagtgcctt tgcagttgca gaagcacgaa atgtattgat ggtggtttct gttggtaacg 1440
tatattacca acacgggaaa cgaagaaaca ttgacaatca cgtcgtcgta cccgccatgt 1500
acagcaaata tttcctcaat gttttaaccg tatccgggat gcaagttacg agcgaagcta 1560
ccattaggga acgtgtcgag cgatgcaagt taacgaagcc ggacgcttcc tgcgaaccca 1620
gcaaagatct acaatatgaa ctgtaccaca agtctcagtt tgggctttca ctcagccagc 1680
tagtggctcc ggcgtacagt atacacacct tatggaagaa taactctaag gttattgctg 1740
agggggtgtc aatggctact gcaattgtga cgggtgttgc aagtctactt ctttccatag 1800
atatgaagtt cctacaactc acctcagtca gcgtcaccca ctatatacgg cacaacatca 1860
tgccacttcc tgcgcttaag aataaggtga gatggggagg atatgtcaat tgccgtgcga 1920
ctgtaatcag tatggtgcaa tataatagag ccctggctga aaggcacaag agaatgaagg 1980
ccatggttct gccacctagg aaaagtgata aggtcaatat tattatctag ataaaaaaaa 2040
aaaaaaaaaa a                                                                  2051

<210> SEQ ID NO 3
<211> LENGTH: 24
<212> TYPE: DNA
<213> ORGANISM: Artificial
<220> FEATURE:
<223> OTHER INFORMATION: Primer sequence for bdsub-1 gene

<400> SEQUENCE: 3
actacagaga ggccaccgaa cggc                                                    24

<210> SEQ ID NO 4
<211> LENGTH: 24
<212> TYPE: DNA
<213> ORGANISM: Artificial
<220> FEATURE:
<223> OTHER INFORMATION: Primer for the bdsub-1 gene

<400> SEQUENCE: 4 tcactttttcc taggtggcag aacc                                                   24

<210> SEQ ID NO 5
<211> LENGTH: 25
<212> TYPE: DNA
<213> ORGANISM: Artificial
<220> FEATURE:
<223> OTHER INFORMATION: Primer for bdsub-1 gene

<400> SEQUENCE: 5
agccgcccat acgatggtta aaagc                                                   25

<210> SEQ ID NO 6
<211> LENGTH: 26
<212> TYPE: DNA
<213> ORGANISM: Artificial
<220> FEATURE:
<223> OTHER INFORMATION: Primer for bdsub-1 gene

<400> SEQUENCE: 6
atctagataa taatattgac cttatc                                                  26

<210> SEQ ID NO 7
<211> LENGTH: 24
<212> TYPE: DNA
<213> ORGANISM: Artificial
<220> FEATURE:
<223> OTHER INFORMATION: Primer for bdsub-1 gene

<400> SEQUENCE: 7
ggaacttaac ggcatccaag gcgt                                                    24

<210> SEQ ID NO 8
<211> LENGTH: 16
<212> TYPE: DNA
<213> ORGANISM: Artificial
<220> FEATURE:
<223> OTHER INFORMATION: Primer for bdsub-1 gene

<400> SEQUENCE: 8
atggttaaag ctttga                                                             16

<210> SEQ ID NO 9
<211> LENGTH: 18
<212> TYPE: DNA
<213> ORGANISM: Artificial

```
<220> FEATURE:
<223> OTHER INFORMATION: Primer for bdsub-1 gene

<400> SEQUENCE: 9
cttaacatcg ccgttcgg                                                 18

<210> SEQ ID NO 10
<211> LENGTH: 24
<212> TYPE: DNA
<213> ORGANISM: Artificial
<220> FEATURE:
<223> OTHER INFORMATION: Primer for bdsub-1 gene

<400> SEQUENCE: 10
actacagaga ggccaccgaa cggc                                          24

<210> SEQ ID NO 11
<211> LENGTH: 24
<212> TYPE: DNA
<213> ORGANISM: Artificial
<220> FEATURE:
<223> OTHER INFORMATION: Primer for bdsub-1 gene

<400> SEQUENCE: 11 tcactttttcc taggtggcag aacc                                         24

<210> SEQ ID NO 12
<211> LENGTH: 865
<212> TYPE: PRT
<213> ORGANISM: Neospora caninum

<400> SEQUENCE: 12
```

| Met | Arg | Ala | Ser | His | Ile | Leu | Leu | Ala | Cys | Ser | Val | Leu | Ile | Val | Leu |
|---|---|---|---|---|---|---|---|---|---|---|---|---|---|---|---|
| 1 | | | | 5 | | | | | 10 | | | | | 15 | |

| Leu | Cys | Met | Asp | Ala | Arg | Gly | Leu | Arg | Val | Arg | Lys | Asp | Gly | Asp | Val |
| | | | 20 | | | | | 25 | | | | | 30 | | |

| Leu | Ser | Pro | Lys | Thr | Phe | Gln | Pro | Asp | Gly | Gly | Glu | Asn | Thr | Thr | Asp |
| | | | 35 | | | | | 40 | | | | | 45 | | |

| Pro | Ser | Asp | Ile | Ile | Glu | Glu | Val | Arg | Lys | Val | Glu | Lys | Gln | Val | Glu |
| 50 | | | | | 55 | | | | | 60 | | | | | |

| Ala | Glu | Ala | Ala | Glu | Ile | Ile | Lys | Ala | Arg | Glu | Glu | His | Arg | Gly | Phe |
| 65 | | | | | 70 | | | | | 75 | | | | | 80 |

| Asn | Thr | Leu | Asp | Asp | Gly | Val | Ala | Pro | Glu | Thr | Glu | Gly | Gly | His | Gly |
| | | | | 85 | | | | | 90 | | | | | 95 | |

| Leu | His | Ala | Ser | Glu | Thr | Thr | Pro | Val | Ala | Glu | Leu | Glu | Pro | Gln | Asp |
| | | | 100 | | | | | 105 | | | | | 110 | | |

| Pro | Asp | Arg | Ser | Leu | Lys | Tyr | Pro | Val | Arg | Leu | Leu | Ile | Val | Asp | Lys |
| | | | 115 | | | | | 120 | | | | | 125 | | |

| Pro | Ala | Gly | Asp | Glu | Glu | Glu | Thr | Arg | Pro | Ser | Phe | Val | Gln | Thr | Ala |
| | | | 130 | | | | | 135 | | | | | 140 | | |

| Leu | His | Ser | Glu | Leu | Ala | Gln | Arg | Val | Val | Lys | Glu | Leu | Asn | Gly | His |
| 145 | | | | | 150 | | | | | 155 | | | | | 160 |

| Val | Asp | Val | Leu | Asp | Glu | Ser | Gly | Val | Val | Leu | Val | Asp | Leu | Pro | Ala |
| | | | | 165 | | | | | 170 | | | | | 175 | |

| Asn | Thr | Thr | Asp | Lys | Gln | Leu | Lys | Glu | Val | Ile | Glu | Thr | Ala | Lys | Ala |
| | | | 180 | | | | | 185 | | | | | 190 | | |

| Gln | Gly | Ala | Ile | Val | Glu | Pro | Asp | His | Met | Val | Ser | Ala | Val | His | Thr |
| | | | 195 | | | | | 200 | | | | | 205 | | |

| Ser | Ser | Arg | Glu | Ser | Asn | Asp | Pro | Leu | Leu | His | Glu | Leu | Trp | Ala | Leu |

-continued

```
        210                 215                 220
Asp Pro Leu Asn Met Arg Ala Ala Trp Asp Ile Leu Thr Thr Ala Glu
225                 230                 235                 240

Leu Gly Gly Asp Arg Arg Pro Leu Val Cys Val Val Asp Thr Gly Ile
                245                 250                 255

Asp Tyr Glu His Pro Asp Leu Arg Glu Asn Met Glu Val Asn Gln Val
                260                 265                 270

Glu Leu His Gly Lys Pro Gly Ile Asp Asp Asn Asn Gly Glu Ile
                275                 280                 285

Asp Asp Ile Tyr Gly Ala Asn Met Val Ser Asp Ser Thr Asp Pro Ala
290                 295                 300

Asp Asp His Ser His Gly Thr His Val Ala Gly Thr Ile Gly Ala Arg
305                 310                 315                 320

Gly Asp Asn Gly Val Gly Ile Ala Gly Ile Ala Trp Ala Pro Arg Leu
                325                 330                 335

Ile Ala Cys Lys Phe Leu Asn Ala Arg Gly Arg Gly Phe Asp Ser Asp
                340                 345                 350

Ala Leu Arg Cys Ile Asn Tyr Cys Ala Lys Gly Ala Asp Ile Met
                355                 360                 365

Asn His Ser Trp Ser Gly Ser Asp Ala Ser Glu Ala Leu Arg Gln Ala
        370                 375                 380

Ile Glu Gln Thr Ala Gln Gln Gly Ile Ile His Ile Ala Ala Ala Gly
385                 390                 395                 400

Asn Ser Gly Arg Asp Val Asp Val Thr Pro Asn Tyr Pro Ala Ala Leu
                405                 410                 415

Ser Thr Ala Val Glu Gly Leu Ile Thr Val Gly Asn Met Lys Met Glu
                420                 425                 430

Lys Gln Arg Asp Gly Ser Lys His Phe Ser Leu Ala Glu Ser Ser Asn
                435                 440                 445

Tyr Gly Thr Lys Ser Val Gln Ile Ala Leu Pro Gly Thr Asp Ile Tyr
        450                 455                 460

Ser Thr Ile Pro Val Gln Glu Arg Pro Asp Asp Pro Tyr Gly Trp Lys
465                 470                 475                 480

Thr Gly Thr Ser Met Ala Ala Pro Ala Leu Ser Gly Ile Val Ala Leu
                485                 490                 495

Met Leu Ala Ala Asn Pro Gly Leu Ser Ala Thr Gln Ile Arg Ser Ile
                500                 505                 510

Leu Met Gln Ser Val Asn Arg Thr Pro Glu Leu Ser Thr Arg Val Thr
                515                 520                 525

Trp Gly Ala Met Pro Asp Ala Lys Arg Cys Leu Asp Ala Ala Leu Val
        530                 535                 540

Thr Pro Pro Glu Gly Arg Arg Pro Gly Asn Pro Ser His Pro Pro
545                 550                 555                 560

Pro Glu Ala Ser Pro Glu Ser Ser Pro Asp Arg Gln His Pro
                565                 570                 575

His Pro His Pro Pro Arg Pro Asn Pro Glu Ala Ser Pro Pro Glu
                580                 585                 590

Pro Ser Pro Pro Asn Trp Gln His Pro His Pro Pro Arg Pro
        595                 600                 605

Asn Pro Pro Glu Ala Ser Pro Pro Glu Pro Ser Pro Pro Asn Trp Gln
610                 615                 620

His Pro His Pro His Pro Pro Arg Pro Asn Pro Pro Gly Ala Ser Pro
625                 630                 635                 640
```

```
Pro Glu Ser Ser Pro Asn Trp Gln His Pro His Pro Pro
            645                 650                 655

Arg Pro Asn Pro Pro Glu Ala Ser Pro Pro Gln Ser Ser Pro Pro Glu
            660                 665                 670

Pro Gln Arg Pro Phe Ser Gln Trp Pro His Thr Pro His Phe Phe His
            675                 680                 685

Tyr His Pro Tyr Pro Gly Tyr Asn Leu Pro Tyr Phe Thr Tyr His Gln
        690                 695                 700

Ser Pro Leu Pro Tyr Gly Pro Tyr Gly Arg Asp Pro Cys Pro Cys Ala
705                 710                 715                 720

Ser His Pro Tyr Pro Ala Asp Asp Ser Pro Leu Gly Ser Tyr Ala Pro
                725                 730                 735

Asp Pro Ser Pro Gln Ser Tyr Pro Pro Glu Pro Ser Pro Ser Lys
            740                 745                 750

Pro Ser Pro Pro Glu Gly Ser Ser Pro Arg Val Pro Ser Pro His Arg
            755                 760                 765

His Pro Ser Arg Ser Arg Leu Pro Ser Ala Val Glu Pro Ser Pro Pro
    770                 775                 780

Pro Ala Ser Pro Gln Pro Ser Pro His Pro Ser Pro Asp Thr Ser
785                 790                 795                 800

Pro Thr Lys Pro Ser Thr Pro Pro Ser Pro Ser Gln Asp Pro Glu
                805                 810                 815

Gly Arg Arg Glu Pro Ser Glu Glu Asp Asp His Lys Ser Leu Ser Asp
                820                 825                 830

Lys Ser Thr Ser His Ser Ser Glu Gly His Ala Gly Ala Thr Pro Leu
                835                 840                 845

Ala Arg Val Gly Val Leu Ala Val Phe Leu Thr Val Val Gly Leu Ile
            850                 855                 860

Val
865

<210> SEQ ID NO 13
<211> LENGTH: 689
<212> TYPE: PRT
<213> ORGANISM: Plasmodium falciparum

<400> SEQUENCE: 13

Met Leu Asn Lys Lys Val Val Ala Leu Cys Thr Leu Thr Leu His Leu
1               5                   10                  15

Phe Cys Ile Phe Leu Cys Leu Gly Lys Glu Val Arg Ser Glu Glu Asn
                20                  25                  30

Gly Lys Ile Gln Asp Asp Ala Lys Lys Ile Val Ser Glu Leu Arg Phe
            35                  40                  45

Leu Glu Lys Val Glu Asp Val Ile Glu Lys Ser Asn Ile Gly Gly Asn
50                  55                  60

Glu Val Asp Ala Asp Glu Asn Ser Phe Asn Pro Asp Thr Glu Val Pro
65                  70                  75                  80

Ile Glu Glu Ile Glu Ile Lys Met Arg Glu Leu Lys Asp Val Lys
                85                  90                  95

Glu Glu Lys Asn Lys Asn Asp Asn His Asn Asn Asn Asn Asn Asn
            100                 105                 110

Asn Ile Ser Ser Ser Ser Ser Ser Asn Thr Phe Gly Glu Glu
        115                 120                 125

Lys Glu Glu Val Ser Lys Lys Lys Lys Leu Arg Leu Ile Val Ser
```

-continued

```
            130                 135                 140
Glu Asn His Ala Thr Thr Pro Ser Phe Phe Gln Glu Ser Leu Leu Glu
145                 150                 155                 160

Pro Asp Val Leu Ser Phe Leu Glu Ser Lys Gly Asn Leu Ser Asn Leu
                165                 170                 175

Lys Asn Ile Asn Ser Met Ile Ile Glu Leu Lys Glu Asp Thr Thr Asp
            180                 185                 190

Asp Glu Leu Ile Ser Tyr Ile Lys Ile Leu Glu Glu Lys Gly Ala Leu
                195                 200                 205

Ile Glu Ser Asp Lys Leu Val Ser Ala Asp Asn Ile Asp Ile Ser Gly
210                 215                 220

Ile Lys Asp Ala Ile Arg Arg Gly Glu Glu Asn Ile Asp Val Asn Asp
225                 230                 235                 240

Tyr Lys Ser Met Leu Glu Val Glu Asn Asp Ala Glu Asp Tyr Asp Lys
                245                 250                 255

Met Phe Gly Met Phe Asn Glu Ser His Ala Ala Thr Ser Lys Arg Lys
                260                 265                 270

Arg His Ser Thr Asn Glu Arg Gly Tyr Asp Thr Phe Ser Ser Pro Ser
            275                 280                 285

Tyr Lys Thr Tyr Ser Lys Ser Asp Tyr Leu Tyr Asp Asp Asn Asn
            290                 295                 300

Asn Asn Asn Tyr Tyr Tyr Ser His Ser Ser Asn Gly His Asn Ser Ser
305                 310                 315                 320

Ser Arg Asn Ser Ser Ser Arg Ser Arg Pro Gly Lys Tyr His Phe
                325                 330                 335

Asn Asp Glu Phe Arg Asn Leu Gln Trp Gly Leu Asp Leu Ser Arg Leu
            340                 345                 350

Asp Glu Thr Gln Glu Leu Ile Asn Glu His Gln Val Met Ser Thr Arg
                355                 360                 365

Ile Cys Val Ile Asp Ser Gly Ile Asp Tyr Asn His Pro Asp Leu Lys
            370                 375                 380

Asp Asn Ile Glu Leu Asn Leu Lys Glu Leu His Gly Arg Lys Gly Phe
385                 390                 395                 400

Asp Asp Asp Asn Asn Gly Ile Val Asp Ile Tyr Gly Ala Asn Phe
                405                 410                 415

Val Asn Asn Ser Gly Asn Pro Met Asp Asp Asn Tyr His Gly Thr His
                420                 425                 430

Val Ser Gly Ile Ile Ser Ala Ile Gly Asn Asn Ile Gly Val Val
            435                 440                 445

Gly Val Asp Val Asn Ser Lys Leu Ile Ile Cys Lys Ala Leu Asp Glu
450                 455                 460

His Lys Leu Gly Arg Leu Gly Asp Met Phe Lys Cys Leu Asp Tyr Cys
465                 470                 475                 480

Ile Ser Arg Asn Ala His Met Ile Asn Gly Ser Phe Ser Phe Asp Glu
                485                 490                 495

Tyr Ser Gly Ile Phe Asn Ser Ser Val Glu Tyr Leu Gln Arg Lys Gly
            500                 505                 510

Ile Leu Phe Phe Val Ser Ala Ser Asn Cys Ser His Pro Lys Ser Ser
            515                 520                 525

Thr Pro Asp Ile Arg Lys Cys Asp Leu Ser Ile Asn Ala Lys Tyr Pro
            530                 535                 540

Pro Ile Leu Ser Thr Val Tyr Asp Asn Val Ile Ser Val Ala Asn Leu
545                 550                 555                 560
```

```
Lys Lys Asn Asp Asn Asn Asn His Tyr Ser Leu Ser Ile Asn Ser Phe
            565                 570                 575

Tyr Ser Asn Lys Tyr Cys Gln Leu Ala Ala Pro Gly Thr Asn Ile Tyr
            580                 585                 590

Ser Thr Ala Pro His Asn Ser Tyr Arg Lys Leu Asn Gly Thr Ser Met
            595                 600                 605

Ala Ala Pro His Val Ala Ala Ile Ala Ser Leu Ile Phe Ser Ile Asn
            610                 615                 620

Pro Asp Leu Ser Tyr Lys Lys Val Ile Gln Ile Leu Lys Asp Ser Ile
625                 630                 635                 640

Val Tyr Leu Pro Ser Leu Lys Asn Met Val Ala Trp Ala Gly Tyr Ala
            645                 650                 655

Asp Ile Asn Lys Ala Val Asn Leu Ala Ile Lys Ser Lys Lys Thr Tyr
            660                 665                 670

Ile Asn Ser Asn Ile Ser Asn Lys Trp Lys Lys Ser Arg Tyr Leu
            675                 680                 685

His

<210> SEQ ID NO 14
<211> LENGTH: 795
<212> TYPE: PRT
<213> ORGANISM: Toxoplasma gondii

<400> SEQUENCE: 14

Met Gly Ser Ser His Ala Ile Val Ala Cys Ala Ala Leu Ile Val Leu
1               5                   10                  15

Leu Ser Thr Asn Ala Arg Gly Leu Arg Val Arg Lys Asp Lys Asp Val
            20                  25                  30

Leu Leu Ala Thr Ser Phe Leu Ser His His Gly Glu Tyr Gln Asn Pro
            35                  40                  45

Thr Ser Thr Tyr Asn Leu Ile Lys Glu Ile Arg Lys Val Glu Ala Glu
        50                  55                  60

Ile Glu Asp Glu Val Glu Thr Leu Asn Arg Asp Arg Arg Leu His Arg
65                  70                  75                  80

Gly His Asn Lys Tyr Ala Asp Asp Ile Arg Gln Gly Leu Lys Asp
                85                  90                  95

Glu Gln Asp Met Gly Ala Ser Glu Asn Ile Pro Val Ala Glu Leu Glu
            100                 105                 110

Pro Gln Asp Leu Asp Arg Glu Ala Lys Tyr Pro Val Arg Met Leu Ile
            115                 120                 125

Val Asp Lys Arg Ser Asp Asp Asp Glu Glu Thr Lys Thr Ser
130                 135                 140

Phe Val Glu Thr Ala Leu His Ser Asp Leu Ala Gln Arg Val Val Lys
145                 150                 155                 160

Glu Leu Asn Gly His Val Asp Val Leu Arg Glu Ser Gly Val Val Leu
            165                 170                 175

Val Asp Leu Pro Ala Gln Thr Thr Asp Lys Gln Leu Gln Glu Leu Ile
            180                 185                 190

Glu Thr Ala Arg Ala Gln Gly Thr Ile Val Glu Pro Asp His Leu Val
            195                 200                 205

Gln Ser Val Asn Thr Ser Ser Lys Gly Ser Asn Asp Pro Leu Leu Asp
            210                 215                 220

Arg Leu Trp Gly Met Asp Ala Leu Asn Val Lys Gly Ala Trp Asp Ile
225                 230                 235                 240
```

```
Ile Thr Thr Gly Glu Pro Asn Met Gly Ser Arg Arg Pro Leu Val Cys
            245                 250                 255

Val Leu Asp Thr Gly Ile Asp Tyr Asn His Pro Asp Leu Arg Asp Asn
            260                 265                 270

Met Glu Val Asn Gln Ala Glu Arg Asp Gly Thr Pro Gly Val Asp Asp
            275                 280                 285

Asp Asn Asn Gly Glu Val Asp Asp Ile Tyr Gly Ala Asn Met Leu Ser
            290                 295                 300

Lys Glu Asn Asp Pro Ala Asp Asp His Ser His Gly Thr His Val Ala
305                 310                 315                 320

Gly Thr Ile Gly Ala His Gly Asn Asn Gly Ile Gly Val Ala Gly Val
                325                 330                 335

Ala Trp Ala Pro Arg Leu Leu Pro Cys Lys Phe Leu Ala Tyr Thr Gly
                340                 345                 350

Arg Gly Tyr Ser Ser Asp Ala Val Arg Cys Ile Asp Tyr Cys Val Lys
                355                 360                 365

Arg Gly Ala Asp Ile Val Asn His Ser Trp Gly Gly Ser Trp Pro Ser
            370                 375                 380

Glu Ala Leu Arg Glu Ala Val Val Arg Thr Ala Asn Asn Gly Leu Ile
385                 390                 395                 400

His Ile Phe Ala Ala Gly Asn Asp Gly Val Asp Ile Asp Gln Arg Ala
                405                 410                 415

Phe Tyr Pro Ala Ala Phe Ser Thr Glu Ala Asp Gly Leu Ile Thr Val
                420                 425                 430

Ala Asn Val Lys Gly Asp Pro Asp His Gly Gly Lys Arg Ile Ile Glu
                435                 440                 445

Leu Asp Arg Ser Ser Asn Tyr Gly Ile Gln Arg Val Gln Val Ala Cys
            450                 455                 460

Pro Gly Met Trp Ile Leu Ser Thr Val Pro Thr Ser Gly Ser Ser Gln
465                 470                 475                 480

Gln Pro Tyr Ala Glu Lys Ser Gly Thr Ser Met Ala Ala Pro Ala Leu
                485                 490                 495

Ser Gly Ile Val Ala Leu Met Leu Ala Val Asn Pro Gly Leu Ser Thr
                500                 505                 510

Arg Gln Val Arg Glu Gly Leu Arg Gln Cys Ser Val Gln Gln Pro Leu
                515                 520                 525

Leu Gln Gly Lys Val Glu Trp Gly Ser Met Pro Asp Ala Lys Arg Cys
            530                 535                 540

Val Glu Tyr Ala Leu Thr Thr His Ala Glu Gly Arg His Lys Ser Phe
545                 550                 555                 560

Arg Arg Glu Pro Ser Thr Glu Thr Ser Thr Pro Pro Ser Pro Ser Pro
                565                 570                 575

Ala Gln Pro Thr Pro Gln Pro Gln Pro His Pro Pro Gln Pro Gln Glu
                580                 585                 590

Thr Pro Pro Ser Ala Pro Ser Pro Pro Thr Pro Pro Ser Ala
                595                 600                 605

Pro Ser Pro Ser Pro Arg Thr Pro Ser Ala Pro Ser Pro Ser Pro
            610                 615                 620

Arg Thr Pro Pro Cys Ala Pro Ser Pro Pro Pro Thr Pro Pro Cys
625                 630                 635                 640

Ala Pro Ser Pro Ser Pro Pro Thr Pro Pro Gly Ser Pro His Lys
                645                 650                 655
```

-continued

```
Pro Glu Pro Gln Thr Pro Val Tyr Pro Glu Val Pro Arg Ser Thr Arg
            660                 665                 670

Ser Pro Pro Pro Ser Pro Pro Thr Glu Ser Ala Pro Gly Ala Pro
        675                 680                 685

Pro Ser Asp Thr Pro Ser Cys Arg Val Pro Pro Cys Ser Ser Ser Pro
            690                 695                 700

Arg Ser Gly Ser Gln Pro Lys Pro Pro Gln Asp Asn Thr Thr Thr Pro
705                 710                 715                 720

Lys Met Pro Ser Leu Ser Ser Pro Pro Thr Glu His Ser Thr Ala Gln
                725                 730                 735

Pro Pro Lys His Glu Asn Asp Ala Arg Glu Glu Glu Pro Pro Thr Asp
            740                 745                 750

Glu Asp Asp Phe Ser Ser Val Lys Gly Lys Lys Leu Gly Ala Tyr Glu
            755                 760                 765

Ser Asp Gly Ser Pro Arg Ala Ser Ser Cys Ala Gly Ala Gly Val Leu
            770                 775                 780

Gly Val Phe Phe Met Val Val Gly Leu Thr Val
785                 790                 795
```